US011382957B2

(12) United States Patent
Sauerberg et al.

(10) Patent No.: US 11,382,957 B2
(45) Date of Patent: *Jul. 12, 2022

(54) SOLID COMPOSITIONS COMPRISING A GLP-1 AGONIST AND A SALT OF N-(8-(2-HYDROXYBENZOYL)AMINO)CAPRYLIC ACID

(71) Applicant: Novo Nordisk A/S, Bagsvaerd (DK)

(72) Inventors: Per Sauerberg, Farum (DK); Simon Bjerregaard, Hilleroed (DK); Flemming Seier Nielsen, Frederikssund (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/180,370

(22) Filed: Feb. 19, 2021

(65) Prior Publication Data

US 2021/0177944 A1 Jun. 17, 2021

Related U.S. Application Data

(63) Continuation of application No. 16/118,381, filed on Aug. 30, 2018, now Pat. No. 10,960,052, which is a continuation of application No. 15/019,412, filed on Feb. 9, 2016, now Pat. No. 10,086,047, which is a continuation of application No. 13/994,262, filed as application No. PCT/EP2011/073060 on Dec. 16, 2011, now Pat. No. 9,278,123.

(60) Provisional application No. 61/425,087, filed on Dec. 20, 2010.

(30) Foreign Application Priority Data

Dec. 16, 2010 (EP) .................................... 10195285

(51) Int. Cl.

| A61P 3/04 | (2006.01) |
|---|---|
| A61P 3/10 | (2006.01) |
| A61K 9/20 | (2006.01) |
| A61K 38/26 | (2006.01) |
| A61K 9/00 | (2006.01) |
| A61K 45/06 | (2006.01) |
| A61K 47/18 | (2017.01) |
| A61K 31/195 | (2006.01) |

(52) U.S. Cl.
CPC ............ *A61K 38/26* (2013.01); *A61K 9/0053* (2013.01); *A61K 9/2013* (2013.01); *A61K 9/2077* (2013.01); *A61K 31/195* (2013.01); *A61K 45/06* (2013.01); *A61K 47/18* (2013.01)

(58) Field of Classification Search
CPC combination set(s) only.
See application file for complete search history.

(56) References Cited

U.S. PATENT DOCUMENTS

| 5,545,618 | A | 8/1996 | Buckley et al. |
|---|---|---|---|
| 5,574,010 | A | 11/1996 | McFadden |
| 5,604,203 | A | 2/1997 | Balasubramaniam |
| 5,773,647 | A | 6/1998 | Leone-Bay et al. |
| 5,866,536 | A | 2/1999 | Leone-Bay et al. |
| 5,968,899 | A | 10/1999 | Sekine et al. |
| 6,046,167 | A | 4/2000 | Balasubramaniam |
| 6,071,510 | A | 6/2000 | Leone-Bay et al. |
| 6,268,343 | B1 | 7/2001 | Knudsen et al. |
| 6,348,447 | B1 | 2/2002 | Hellstrom et al. |
| 6,458,924 | B2 | 10/2002 | Knudsen et al. |
| 7,049,283 | B2 | 5/2006 | Ault et al. |
| 7,235,627 | B2 | 6/2007 | Knudson et al. |
| 7,271,149 | B2 | 9/2007 | Glaesner et al. |
| 7,417,028 | B2 | 8/2008 | Ewing et al. |
| 8,022,035 | B2 | 9/2011 | Schwartz et al. |
| 8,039,018 | B2 | 10/2011 | Majuru et al. |
| 8,053,429 | B2 | 11/2011 | Cumming et al. |
| 8,097,698 | B2 | 1/2012 | Knudsen et al. |
| 8,536,122 | B2 | 9/2013 | Lau et al. |
| 8,648,041 | B2 | 2/2014 | Garibay et al. |
| 8,895,694 | B2 | 11/2014 | Spetzler et al. |
| 8,901,073 | B2 | 12/2014 | Bloom |
| 9,067,977 | B2 | 6/2015 | Spetzler et al. |
| 9,085,637 | B2 | 7/2015 | Oestergaard et al. |
| 9,186,392 | B2 | 11/2015 | Klein et al. |
| 9,266,940 | B2 | 2/2016 | Wieczorek et al. |
| 9,278,123 | B2 | 3/2016 | Sauerberg et al. |
| 9,527,900 | B2 | 12/2016 | Linderoth et al. |
| 9,993,430 | B2 | 6/2018 | Jensen et al. |
| 10,086,047 | B2 | 10/2018 | Sauerberg et al. |
| 10,246,497 | B2 | 4/2019 | Oestergaard et al. |
| 10,278,923 | B2 | 5/2019 | Nielsen et al. |

(Continued)

FOREIGN PATENT DOCUMENTS

| CN | 1190893 A | 8/1998 |
|---|---|---|
| CN | 1867360 A | 11/2006 |

(Continued)

OTHER PUBLICATIONS

Wang et al., "Non-peptidic glucose-like peptide-1 receptor agonists: aftermath of a serendipitous discovery," Acta Pharamcol. Sinica 31:1026-1030 (2010) (Year: 2010).*

Beglinger C et al., Clinical Pharmacology and Therapeutics,"Pharmacokinetics and Pharmacodynamic Effects of Oral GLP-1 and PYY3-36: A Proof-Of-Concept Study in Healthy Subjects"., 2008, vol. 84, No. 4, pp. 468-474.

Steinert RE et al, American Journal of Clinical Nutrition,"Oral Administration of Glucagon-Like Peptide 1 or Peptide YY 3-36 Affects Food Intake in Healthy Male Subjects", 2010, vol. 92, pp. 810-817.

(Continued)

*Primary Examiner* — Julie Ha
*Assistant Examiner* — Kristina M Hellman
(74) *Attorney, Agent, or Firm* — Leon Y. Lum

(57) ABSTRACT

The present invention relates to solid compositions comprising a GLP-1 agonist and a salt of N-(8-(2-hydroxybenzoyl)amino)caprylic acid and their use in medicine.

9 Claims, No Drawings

Specification includes a Sequence Listing.

(56) References Cited

U.S. PATENT DOCUMENTS

| | | |
|---|---|---|
| 10,335,369 B2 | 7/2019 | Vilhelmsen |
| 10,960,052 B2 | 3/2021 | Sauerberg et al. |
| 11,117,947 B2 | 9/2021 | Wieczorek et al. |
| 2001/0011071 A1 | 8/2001 | Knudsen et al. |
| 2002/0141985 A1 | 10/2002 | Pillner et al. |
| 2005/0009748 A1 | 1/2005 | Dinh et al. |
| 2005/0148497 A1 | 7/2005 | Khan |
| 2005/0176630 A1 | 8/2005 | Cowley et al. |
| 2006/0078622 A1 | 4/2006 | Majuru et al. |
| 2006/0078623 A1 | 4/2006 | Dhoot et al. |
| 2006/0135747 A1 | 6/2006 | Levy et al. |
| 2006/0211610 A1 | 9/2006 | Dong |
| 2006/0286129 A1 | 12/2006 | Sarubbi |
| 2007/0049557 A1 | 3/2007 | Ahmed et al. |
| 2007/0135351 A1 | 6/2007 | Conde-Knape et al. |
| 2007/0197445 A1 | 8/2007 | Balasubramaniam |
| 2007/0203058 A1 | 8/2007 | Lau et al. |
| 2007/0224262 A1 | 9/2007 | Majuru et al. |
| 2008/0076705 A1 | 3/2008 | Kodra et al. |
| 2008/0153779 A1 | 6/2008 | Liao et al. |
| 2008/0194486 A1 | 8/2008 | Bridon et al. |
| 2008/0194676 A1 | 8/2008 | Abbas et al. |
| 2008/0207507 A1 | 8/2008 | Lau et al. |
| 2008/0221038 A1 | 9/2008 | Balasubramaniam |
| 2008/0255250 A1 | 10/2008 | Gomez-Orellana et al. |
| 2008/0269114 A1 | 10/2008 | Schwartz |
| 2009/0088369 A1 | 4/2009 | Steiness |
| 2009/0099074 A1 | 4/2009 | Bridon et al. |
| 2009/0111730 A1 | 4/2009 | Dorwald et al. |
| 2009/0124639 A1 | 5/2009 | Oyewumi et al. |
| 2009/0143330 A1 | 6/2009 | Levchik et al. |
| 2009/0156478 A1 | 6/2009 | Lau et al. |
| 2009/0186811 A1 | 7/2009 | Schwartz |
| 2009/0215682 A1 | 8/2009 | Moore et al. |
| 2010/0016229 A1 | 1/2010 | Sarubbi |
| 2010/0069307 A1 | 3/2010 | Danho et al. |
| 2010/0069410 A1 | 3/2010 | Majuru et al. |
| 2010/0151009 A1 | 6/2010 | Levchik |
| 2010/0210526 A1 | 8/2010 | Joshi |
| 2010/0239658 A1 | 9/2010 | Majuru et al. |
| 2010/0292133 A1 | 11/2010 | Spetzler et al. |
| 2010/0331245 A1 | 12/2010 | Dong |
| 2011/0142800 A1 | 6/2011 | Kidron et al. |
| 2011/0166321 A1 | 7/2011 | Garibay et al. |
| 2011/0218148 A1 | 9/2011 | Azria et al. |
| 2011/0275559 A1 | 11/2011 | Ostergaard et al. |
| 2012/0040893 A1 | 2/2012 | Cowley et al. |
| 2013/0040877 A1 | 2/2013 | Kofoed et al. |
| 2013/0053311 A1 | 2/2013 | Kalthoff et al. |
| 2013/0096055 A1 | 4/2013 | Kofoed et al. |
| 2013/0240587 A1 | 9/2013 | Buchhalter |
| 2013/0345134 A1 | 12/2013 | Sauerberg et al. |
| 2014/0011732 A1 | 1/2014 | Spetzler et al. |
| 2014/0296131 A1 | 10/2014 | Spetzler et al. |
| 2015/0025003 A1 | 1/2015 | Spetzler et al. |
| 2015/0031606 A1 | 1/2015 | Vilhelmsen |
| 2015/0072926 A1 | 3/2015 | Vilhelmsen et al. |
| 2015/0141336 A1 | 5/2015 | Joergensen et al. |
| 2015/0150811 A1 | 6/2015 | Jensen et al. |
| 2016/0067184 A1 | 3/2016 | Nielsen et al. |
| 2016/0151462 A1 | 6/2016 | Sauerberg et al. |
| 2016/0263197 A1 | 9/2016 | Oestergaard et al. |
| 2016/0289283 A1 | 10/2016 | Oestergaard et al. |
| 2017/0312225 A1 | 11/2017 | Nielsen et al. |
| 2017/0313750 A1 | 11/2017 | Oestergaard et al. |
| 2018/0021272 A1 | 1/2018 | Burshtein et al. |
| 2018/0028622 A1 | 2/2018 | Burshtein et al. |
| 2018/0036234 A1 | 2/2018 | Burshtein et al. |
| 2018/0036382 A1 | 2/2018 | Burshtein et al. |
| 2018/0050096 A1 | 2/2018 | Burshtein et al. |
| 2018/0235888 A1 | 8/2018 | Jensen et al. |
| 2018/0251512 A1 | 9/2018 | Wieczorek et al. |
| 2018/0360918 A1 | 12/2018 | Sauerberg et al. |
| 2019/0216739 A1 | 7/2019 | Nielsen et al. |
| 2019/0231876 A1 | 8/2019 | Pedersen et al. |
| 2019/0314283 A1 | 10/2019 | Vilhelmsen |
| 2020/0000728 A1 | 1/2020 | Pedersen et al. |
| 2020/0079834 A1 | 3/2020 | Wieczorek et al. |
| 2021/0275458 A1 | 5/2021 | Bjerregaard et al. |

FOREIGN PATENT DOCUMENTS

| | | |
|---|---|---|
| CN | 101005857 A | 7/2007 |
| CN | 101010339 A | 8/2007 |
| CN | 101133082 A | 2/2008 |
| CN | 101268099 A | 9/2008 |
| CN | 101463081 A | 6/2009 |
| CN | 102946875 A | 2/2013 |
| EP | 0708179 A2 | 4/1996 |
| EP | 0908515 A2 | 4/1999 |
| EP | 1364967 A2 | 11/2003 |
| EP | 2565202 A1 | 3/2013 |
| EP | 2651398 A1 | 10/2013 |
| JP | 05-506427 | 9/1993 |
| JP | H05-506427 A | 9/1993 |
| JP | 2001-504105 A | 3/2001 |
| JP | 2004131398 A | 4/2004 |
| JP | 2006-520818 A | 9/2006 |
| JP | 2007-536268 A | 12/2007 |
| JP | 2008-509933 A | 4/2008 |
| JP | 2009542711 A | 12/2009 |
| JP | 2010-530962 A | 9/2010 |
| JP | 2011509077 A | 3/2011 |
| JP | 2012-121923 A | 6/2012 |
| JP | 2013543814 A | 12/2013 |
| JP | 2014503526 A | 2/2014 |
| JP | 2015-515459 A | 5/2015 |
| KR | 20060100428 A | 9/2006 |
| KR | 102072202 | 1/2020 |
| NZ | 219575 A | 4/1990 |
| RU | 2158138 C2 | 10/2000 |
| RU | 2226402 C2 | 4/2004 |
| RU | 2275207 C2 | 4/2006 |
| WO | 111457 | 8/1991 |
| WO | 9614854 A1 | 5/1996 |
| WO | 96/29342 | 9/1996 |
| WO | 9725064 | 7/1997 |
| WO | 9808871 A1 | 3/1998 |
| WO | 9820885 A1 | 5/1998 |
| WO | 9820895 | 5/1998 |
| WO | 99/43705 A1 | 9/1999 |
| WO | 99/43706 A1 | 9/1999 |
| WO | 99/43707 A1 | 9/1999 |
| WO | 99/43708 A1 | 9/1999 |
| WO | 9964394 A1 | 12/1999 |
| WO | 00/07617 A1 | 2/2000 |
| WO | 00/16797 A2 | 3/2000 |
| WO | 00/34331 | 6/2000 |
| WO | 200048589 A1 | 8/2000 |
| WO | 200050012 A1 | 8/2000 |
| WO | 00/69911 | 11/2000 |
| WO | 0066629 A1 | 11/2000 |
| WO | 01/04156 | 1/2001 |
| WO | 0124777 A1 | 4/2001 |
| WO | 200141737 A2 | 6/2001 |
| WO | 02/46227 A2 | 6/2002 |
| WO | 02/47712 A2 | 6/2002 |
| WO | 0248192 A2 | 6/2002 |
| WO | 03/002158 A1 | 1/2003 |
| WO | 2003005944 A1 | 1/2003 |
| WO | 03/011892 A2 | 2/2003 |
| WO | 03063838 A1 | 8/2003 |
| WO | 03/072195 A2 | 9/2003 |
| WO | 2004/067548 A2 | 8/2004 |
| WO | 04/066966 A2 | 8/2004 |
| WO | 2004093823 A2 | 11/2004 |
| WO | 2004/104018 A2 | 12/2004 |
| WO | 2005/005667 A2 | 1/2005 |
| WO | 2005004900 A1 | 1/2005 |
| WO | 2005/014035 A2 | 2/2005 |
| WO | 2005014049 A2 | 2/2005 |
| WO | 2005/027978 A2 | 3/2005 |
| WO | 2005/028516 A2 | 3/2005 |
| WO | 2005/058954 A1 | 6/2005 |

(56) References Cited

FOREIGN PATENT DOCUMENTS

| | | |
|---|---|---|
| WO | 2005/058958 A2 | 6/2005 |
| WO | 2005049061 A2 | 6/2005 |
| WO | 2005/077072 A2 | 8/2005 |
| WO | 2005/077094 A2 | 8/2005 |
| WO | 2005/089786 A2 | 9/2005 |
| WO | 2005/089789 A2 | 9/2005 |
| WO | 2005/089790 A2 | 9/2005 |
| WO | 2005099672 A1 | 10/2005 |
| WO | 2005107462 A2 | 11/2005 |
| WO | 2005107773 A2 | 11/2005 |
| WO | 2005/117984 A2 | 12/2005 |
| WO | 2005/121090 A1 | 12/2005 |
| WO | 2006/005667 A2 | 1/2006 |
| WO | 2006/017251 A2 | 2/2006 |
| WO | 06020207 A2 | 2/2006 |
| WO | 2006/037810 | 4/2006 |
| WO | 06/049681 A2 | 5/2006 |
| WO | 2006/077035 A1 | 7/2006 |
| WO | 2006/082204 A1 | 8/2006 |
| WO | 2006084164 A2 | 8/2006 |
| WO | 2006/097535 A2 | 9/2006 |
| WO | 2006/097536 A2 | 9/2006 |
| WO | 2006/097537 A2 | 9/2006 |
| WO | 2006/097538 | 9/2006 |
| WO | 2006/097538 A1 | 9/2006 |
| WO | 2006096515 A2 | 9/2006 |
| WO | 2006097537 A2 | 9/2006 |
| WO | 2006103661 A2 | 10/2006 |
| WO | 2006/127948 A2 | 11/2006 |
| WO | 2006124047 A2 | 11/2006 |
| WO | 2006124047 A3 | 11/2006 |
| WO | 2007/009894 A2 | 1/2007 |
| WO | 2007008778 A2 | 1/2007 |
| WO | 2007011958 A2 | 1/2007 |
| WO | 2007024700 A2 | 3/2007 |
| WO | 2007/038943 A1 | 4/2007 |
| WO | 2007038942 A1 | 4/2007 |
| WO | 2007061434 A2 | 5/2007 |
| WO | 2007/068718 A1 | 6/2007 |
| WO | 07065808 A2 | 6/2007 |
| WO | 2007067964 A2 | 6/2007 |
| WO | 2007093226 A1 | 8/2007 |
| WO | 07109354 A2 | 9/2007 |
| WO | 2007117706 A2 | 10/2007 |
| WO | 2007121318 A2 | 10/2007 |
| WO | 2007/128817 A2 | 11/2007 |
| WO | 2007146234 A2 | 12/2007 |
| WO | 2008/003947 A1 | 1/2008 |
| WO | 2008003050 A2 | 1/2008 |
| WO | 2008020096 A1 | 2/2008 |
| WO | 2008028859 A1 | 3/2008 |
| WO | 2008033888 A2 | 3/2008 |
| WO | 2008039351 A2 | 4/2008 |
| WO | 08/053360 A2 | 5/2008 |
| WO | 2008/087186 A2 | 7/2008 |
| WO | 2008/087190 A2 | 7/2008 |
| WO | 2008109385 A2 | 9/2008 |
| WO | 2008132435 A1 | 11/2008 |
| WO | 2008/154619 A1 | 12/2008 |
| WO | 2009007714 A2 | 1/2009 |
| WO | 2009/030771 A1 | 3/2009 |
| WO | 2009030738 A1 | 3/2009 |
| WO | 2009032749 A2 | 3/2009 |
| WO | 2009033710 A1 | 3/2009 |
| WO | 2009/042922 A2 | 4/2009 |
| WO | 2009/050738 A2 | 4/2009 |
| WO | 09042922 A2 | 4/2009 |
| WO | 2009059188 A1 | 5/2009 |
| WO | 2009/083549 A1 | 7/2009 |
| WO | 2009083549 A1 | 7/2009 |
| WO | 2009/138511 A1 | 11/2009 |
| WO | 2010020978 A1 | 2/2010 |
| WO | 2010/029159 A1 | 3/2010 |
| WO | 10031707 A1 | 3/2010 |
| WO | 2010031521 A2 | 3/2010 |
| WO | 2010/043319 A1 | 4/2010 |
| WO | 2010052144 A2 | 5/2010 |
| WO | 2010/092163 A2 | 8/2010 |
| WO | 2010096175 A1 | 8/2010 |
| WO | 2011/029551 A2 | 3/2011 |
| WO | 11033068 A1 | 3/2011 |
| WO | 2011033068 A1 | 3/2011 |
| WO | 11045232 A2 | 4/2011 |
| WO | 2011058165 A1 | 5/2011 |
| WO | 2011084618 A2 | 7/2011 |
| WO | 2011094531 A1 | 8/2011 |
| WO | 2011109787 A1 | 9/2011 |
| WO | 2011116139 A2 | 9/2011 |
| WO | 2011131646 A1 | 10/2011 |
| WO | 2011138421 A1 | 11/2011 |
| WO | 2012080471 A1 | 6/2012 |
| WO | 2012140117 A1 | 10/2012 |
| WO | 2013009545 A1 | 1/2013 |
| WO | 2013139694 A1 | 9/2013 |
| WO | 2013139695 A1 | 9/2013 |
| WO | 2013189988 A1 | 12/2013 |
| WO | 2014005858 A1 | 1/2014 |
| WO | 2014177683 A1 | 11/2014 |
| WO | 2014178018 A1 | 11/2014 |
| WO | 2015071355 A1 | 5/2015 |
| WO | 2016128970 A1 | 8/2016 |
| WO | 2016128971 A1 | 8/2016 |
| WO | 2016128972 A1 | 8/2016 |
| WO | 2016128973 A1 | 8/2016 |
| WO | 2016128974 A1 | 8/2016 |
| WO | 2016198682 A1 | 12/2016 |
| WO | 2017060500 A1 | 4/2017 |

OTHER PUBLICATIONS

He Xiaorong et al., Mechanistic Study of the Effect of Roller Compaction and Lubricant on Tablet Mechanical Strength, Journal: Journal of Pharmaceutical Sciences,Year: 2007, vol. 96, No. 5, pp. 1342-1355.

Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.

Rowe Raymond C et al., Book: Handbook of Pharmaceutical Excipients, Title: Acesulfame Potassium, Edition—5th, Year: 2006, Complete book.

Steinert R E et al., Orally Administered Glucagon-Like Peptide-1 Affects Glucose Homeostasis Following an Oral Glucose Tolerance Test in Healthy Male Subjects, Journal: Clinical Pharmacology And Therapeutics, Year: 2009, vol. 86, No. 6, pp. 644-650.

Von Eggelkraut-Gottanka Stephan G. et al., Roller Compaction and Tabletting of St. John's Wort Plant Dry Extract Using a Gap Width and Force Controlled Roller; Compactor. IL Study of Roller Compaction Variables on Granule and Tablet Properties by a 33 Factorial Design, Journal: Pharmaceutical Development and Technology, Year: 2002, vol. 7, No. 4, pp. 447-455.

Beglinger C et al., Pharmacokinetics and Pharmacodynamic Effects of Oral GLP-1 and PYY3-36: A Proof-of-concept Study in Healthy Subjects, Journal: Clinical Pharmacology & Therapeutics, Nature Publishing Group, Year 2008. vol. 84, No. 4, pp. 468-474.

Leonard Thomas W et al., Promoting absorption of drugs in humans using medium-chain fatty acid-based solid dosage forms:GIPET™, Journal: Expert Opinion Drug Delivery, Year: 2006, vol. 3(5), pp. 685-692.

Maher Sam et al., Overcoming poor permeability: translating permeation enhancers for oral peptide delivery, Journal Drug Discovery Today:Technologies, Year: 2011, vol. 9, No. 2, pp. e113-e119.

Maher Sam et al., Safety and efficacy of sodium caprate in promoting oral drug absorption: from in vitro to the clinic, Journal: Advanced Drug Delivery Reviews, Year: 2009, vol. 61, pp. 1427-1449.

Michel Marre et al., GLP-1 receptor agonists today, Journal: Diabetes Research; and Clinical Practice, Year: 2011, vol. 93, No. 3, pp. 317-327.

(56) References Cited

OTHER PUBLICATIONS

Walsch Edwin G et al., Oral delivery of macromolecules: rationale underpinning Gastrointestinal Permeation Enhancement Technology (GIPET®), Journal: Therapeutic Delivery, Year: 2011, vol. 2, No. 12, pp. 1595-1610. OTH.
Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.
Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.
Aenugu H.P.R et al. Near Infra Red Spectroscopy—An Overview, "International Journal of ChemTech Research" Year 2011, vol. 3, No. 2, pp. 825-836.
Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.
Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-porf-steffens/download-16, the whole document.
Remington, The Science and Practice of Pharmacy, 22nd Edition, 2012.
Felix Kratz "A Clinical Update of Using Albumin as a Drug Vehicle—A Commentary" Journal of Controlled Release 2014 vol. 190 pp. 331-336.
Rivera et al. Oral Delivery of Heparin in Combination with Sodium N-[8-(2-Hydroxybenzoyl)amino]caprylate: Pharmacological Considerations. Pharmaceutical Research 1997 vol. 14 No. 12 pp. 1830-1834.
Su Young Chae et al. "Preparation, Characterization and Application of Biotinylated and Biotin-PEGylated Glucagon-Like Peptide-1 Analogues for Enhanced Oral Delivery." Bioconjugate Chemistry 2008 vol. 19 No. 1 pp. 334-341.
Emisphere Technologies. "Carriers Enhance Drug Delivery" Manufacturing Chemistry 1999 vol. 70 No. 6 pp. 25-26.
Adam W. G. Alani et al., "Mechanistic Understanding of Oral Drug Absorption Enhancement of Cromolyn Sodium by an Amino Acid Derivative," Pharmaceutical Research, 2008, vol. 25, No. 1, pp. 48-54.
Granulation Handbook, May 30, 1975, 1st Edition First Press, p. 173-197.
Design and evaluation of formulation for oral administration, Feb. 10, 1995, p. 264-279.
Bhansali et al., "Historical Overview of Incretin Based Therapies," Supplement to JAPI, 2010, vol. 58, pp. 10-14.
Valentino et al., "Central and Peripheral Molecular Targets for Antiobesity Pharmacotherapy," Clinical Pharmacology and Therapeutics, 2010, vol. 87, No. 6, pp. 652-662.
Bastin et al., "Salt Selection and Optimisation Procedures for Pharmaceutical New Chemical Entities," Org Proc Res & Devt, 2000, vol. 4, pp. 427-435.
Drug Data Report, 2006, vol. 28, p. 933.
Anonymous, "Eligen@ Technology. Summary and Value Proposition", Emisphere, Feb. 24, 2017, pp. 1-10, URL: https://www.emisphere.com/wp-content/uploads/2017/02/Eligen-Technology-Presentation_2.15-Update.pdf, XP055520567.
Keck et al., Moderne Pharmazeutische Technologie, 2009, pp. 8-14.
Kidron et al., "A Novel Per-Oral Insulin Formulation: Proof of Concept Study in Non-Diabetic Subjects," Diabetic Medicine, 2004, vol. 21, pp. 354-357.
Letter to Sandoz International GmbH regarding English translation of claim of patent JP4585037, dated Aug. 29, 2018.
Mullins, "Statistics for the Quality Control Chemistry Laboratory," 2003, Chapter I, pp. 10-17.
SNAC, Synchem, http://www.synchem.de/product/snac, accessed Aug. 16, 2018.
Valentino et al., "Current Trends in Targeting the Hormonal Regulation of Appetite and Energy Balance to Treat Obesity," Expert Rev Endocrinol Metab, 2010, vol. 5, pp. 765-783.
WHO Drug Information, "International Nonproprietary Names for Pharmaceutical Substances," 2009, vol. 23, No. 2, p. 164.
U.S. Appl. No. 61/425,087, filed Dec. 20, 2010.
EP Application No. 10195285.1, filed Dec. 16, 2010.
Wang et al., "Non-peptidic glucose-like peptide-1 receptor agonists: aftermath of serendipitous discovery," Acta Pharmacol. Sinica, 2010, vol. 31, pp. 1026-1030.
Baynes, Kevin C. R., "The evolving world of GLP-1 agonist therapies for type 2 diabetes" Therapeutic Advances in Endocrinology and Metabolism, 2010,,vol. 1, No. 2, pp. 61-67.
Buckley, Stephen T. et al., "Transcellular stomach absorption of a derivatized glucagon-like peptide-1 receptor agonist" Science Translational Medicine, Nov. 14, 2018, vol. 10, pp. 1-14.
Christensen, Mikkel et al., "Once-Weekly GLP-1 Agonists: How Do They Differ from Exenatide and Liraglutide?" Curr Diab Rep, 2010, vol. 10, pp. 124-132.
Davies, Melanie et al., "Effect of Oral Semaglutide Compared with Placebo and Subcutaneous Semaglutide on Glycemic Control in Patients with Type 2 Diabetes" JAMA, 2017, vol. 318, pp. 1460-1470.
Declaration by the Inventor, Flemming S. Nielsen, dated Feb. 11, 2019.
EMEA Assessment Report EMEA/379172/2009 for Victoza (liraglutide), 2009.
Goldberg, Michael et al., "Challenges for the Oral Delivery of Macromolecules" Nature Reviews Drug Discovery, 2003, vol. 2, pp. 289-294.
Granhall, Charlotte et al., "Safety and Pharmacokinetics of Single and Multiple Ascending Doses of the Novel Oral Human GLP-1 Analogue, Oral Semaglutide, in Healthy Subjects and Subjects with Type 2 Diabetes" Clinical Pharmacokinetics, published Dec. 18, 2018.
Hellriegel, Edward T. et al., "Interpatient variability in bioavailability is related to the extent of absorption: Implications for bioavailability and bioequivalence studies" Clinical Pharmacology & Therapeutics, Dec. 1996, vol. 60, No. 6, pp. 601-607.
Coskun et al., "LY3298176, a novel dual GIP and GLP-1 receptor agonist for the treatment of type 2 diabetes mellitus: From discovery to clinical proof of concept," Molecular Metabolism, 2018, vol. 18, pp. 3-14.
David J. Edmonds et al., "Oral GLP-1 Modulators for the Treatment of Diabetes". Annual Reports in Medicinal Chemistry, 2013, 1st edition, vol. 48, Chapter 9, pp. 119-130.
DJ. Birkett, "Pharmacokinetics made easy 11 Designing dose regimens," Australian Prescriber, 1996, vol. 19, No. 3, pp. 76-88.
E. Mutschler et al., Mutschler Arzneimittelwirkungen, Lehrbuch der Pharmakologie und Toxikologie, 8th edition 2001, pp. 48-51.
Emisphere Annual Report and Proxy 2013, publicly available at the latest on Apr. 17, 2014, 127 pages.
EU Clinical Trials Register Summary EudraCT No. 2012-004994-16 (NN9924-3790), published Jul. 30, 2013, accessed Jun. 7, 2019.
EU Leaflet of Linagliptin, 1st authorization in EU: Aug. 24, 2011 (p. 2, 3 & 13).
EU Leaflet of Linagliptin-Metformin, 1st authorization in EU: Jul. 20, 2012 (p. 2, 3 & 21).
EU Leaflet of Metformin, 1st authorization in EU: Jul. 31, 2001 (p. 1, 2 & 11).
EU Leaflet of Saxagliptin, 1st authorization in EU: Oct. 1, 2009 (p. 1 & 18).
EU Leaflet of Sitagliptin, 1st authorization in EU: Mar. 21, 2007 (p. 2, 3 & 16).
EU Leaflet of Sitagliptin-Metformin, 1st authorization in EU: Jul. 16, 2008 (p. 2, 3 & 20).
EU Leaflet of Vildagliptin, 1st authorization in EU: Sep. 26, 2007(p. 2, 3 & 18).
EU Leaflet of Vildagliptin-Metformin, 1st authorization in EU: Nov. 14, 2007 (p. 2, 3 & 21).
European Patent Application 13166205, filed May 2, 2013.

(56) References Cited

OTHER PUBLICATIONS

Geiser et al., "Clinical Pharmacokinetics of Dulaglutide in Patients with Type 2 Diabetes: Analyses of Data from Clinical Trials". Clinical Pharmacokinetics, 2016, vol. 55, pp. 625-634.
Granhall et al, Safety and Pharmacokinetics of Single and Multiple Ascending Doses of the Novel Oral Human GLP-1 Analogue, Oral Semaglutide, in Healthy Subjects and Subjects with Type 2 Diabetes, Clinical Pharmacokinetics, Dec. 2018.
Leon Shargel, Applied Biopharmaceutics and Pharmacokinetics, 6th edition, 2012, Chapter 8, Multiple-Dosage Regimens, pp. 153-175.
Linda Felton, Remington, Essentials of Pharmaceutics, 2012, Chapter 37, pp. 708-709 and 712-713.
M. Gonzalez Brao, "48th Annual Meeting of the European Association for the Study of Diabetes (EASD)," Drugs of the Future, 2012, vol. 37, No. 12, pp. 871-878.
Malcolm Rowland et al., "Clinical Pharmacokinetics and Pharmacodynamics : Concepts and Applications," Chapter 11—Multiple-Dose Regimens (pp. 293-329); 4th ed.; Philadelphia: Wolters Kluwer Health/Lippincott William & Wilkins, 2011.
Product details regarding David J. Edmonds et al., "Oral GLP-1 Modulators for the Treatment of Diabetes". Annual Reports in Medicinal Chemistry (2013), 1st edition, vol. 48, chapter 9, pp. 119-130, from amazon.com, accessed on May 3, 2019.
Prosecution file of EP2991671B1, available at the EPO Register, the pdf is not attached. https://register.epo.org/application?number=EP14721834&lng=en&tab=doclist, accessed Jun. 14, 2019.
Quianzon et al., "Lixisenatide-Once daily glucagon-like peptide-1 receptor agonist in the management of type 2 diabetes," 2011, US Endocrinology, Diabetes Management, vol. 7, No. 2, pp. 104-109.
Rosenstock et al., "Potential of albiglutide, a long-acting GLP-1 receptor agonist, in type 2 diabetes: a randomized controlled trial exploring weekly, biweekly, and monthly dosing". Diabetes Care, 2009, vol. 32, No. 10, pp. 1880-1886.
S. Dhillon et al., "Basic Pharmacokinetics," Clinical Pharmacokinetics, 2006, Pharmaceutical Press, London; Chapter 1, pp. 1-44.
Sarfaraz K. Niazi, Handbook of Bioequivalence Testing, 2007, p. 13-15.
Schematic overview of sequences and plasma half-life in humans of "GLP-1 peptides" cited as E4 in Sanofi Opposition in EP2991671, dated May 22, 2019.
Sisson, "Liraglutide: clinical pharmacology and considerations for therapy," Pharmacotherapy, 2011, vol. 31, pp. 896-911.
Study NCT01686945, version 1, published Sep. 18, 2012, accessed Jun. 6, 2019.
Study NCT01866748, version 1, published May 31, 2013, accessed Jun. 6, 2019.
Study NCT01923181, version 1, published Aug. 15, 2013, accessed Jun. 5, 2019.
Submission of Novo Nordisk dated Feb. 15, 2019 in response to oppositions against EP2651398B1.
Chae S Y et al., Journal Title: Journal of the Controlled Release,Title: The Fatty Acid Conjugated Exendin-4 Analogs for Type 2 Antidiabetic Therapeutics ,Year: 2010,vol. 144,pp. 10-16.
EP09179390.1 Priority Application Filed on Dec. 16, 2009 by Novo Nordisk.
EP10190515.6 Priority Application Filed on Nov. 9, 2010 by Novo Nordisk.
Dolensky et al., "New Building Blocks for Fluorinated Imidazole," Jorunal of Organic Chemistry, vol. 66(13), pp. 4687-4691 (2001).
Knudsen et al., "Potent Derivatives of Glucagon-Like Peptide-1 With Pharmacokinetic Properties Suitable for Once Daily Administration," Journal of Medicinal Chemistry, 2000, vol. 43(9), pp. 1664-1669.
Dumelin et al.., "A Portable Albumin Binder From a DNA-Encoded Chemical Library", Angewandte Chemie (International Edition in English), vol. 47(17), pp. 3196-3201 (2008).
Rawlay SS et al. Journal of Organic Chemistry. "Oxidation of Primary, Secondary, and Tertiary Amines With Neutral Permanganate. A Simple Method for Degrading Amines to Aldehydes and Ketones." 1967. vol. 32(10). pp. 3129-3131.
Travis B R et al. Organic Letters. "Facile Oxidation of Aldehydes to Acids and Esters With Oxone." 2003. vol. 5(7). pp. 1031-1034.
Murage E N et al. Bioorganic & Medicinal Chemistry. "Search for ¿-Helical Propensity in the Receptor-Bound Conformation of Glucagon-Like Peptide-1." 2008. vol. 16. pp. 10106-10112.
Ruan Guo-Hu et al "Progress of Pharmaceutical Studies on Diabetes" Practical Pharmacy and Clinic, 2007, vol. 10, No. 1, pp. 56-57.
Zheng, "Formulation and Analytical Development for Low-Dose Oral Drug Products," John Wiley & Sons, Inc., 2009, p. 194.
"International Nonproprietary Names for Pharmaceutical Substances (INN)," WHO Drug Information, 2009, vol. 23, No. 2, p. 129.
Rowe et al.,"Sodium Lauryl Sulfate," Handbook of Pharmaceutical Excipients, 6th Edition, 2009, pp. 651-653.
Ajaz S. Hussain, "A Collaborative Search for Efficient Methods of Ensuring Unchanged Product Quality and Performance During Scale-Up of Immediate-Release Solid Oral Dosage Forms," Pharmaceutical Process Scale-Up, 2002, 1st Edition, Chapter 11, pp. 325-352.
Bai et al., Excipient Development for Pharmaceutical, Biotechnology, and Drug Delivery Systems, 2006, Chapter 12, pp. 181-185.
C. M. Keck et al., "Moderne Pharmazeutische Technologie—Lehbuch fur Studierende," 1. Auflage (2009), Kapitel 1.2 H. J. Ji.inginger, "Delivery Systeme fur die perorale Applikation van Peptiden," pp. 1-14.
European Application No. 12172739.0, filed Jun. 20, 2012.
King, Simon, "ViewPoints: Novo Nordisk R&D chief predicts an oral revolution for biologics" Nov. 14, 2018, Available from: [http://www.firstwordpharma.com/print/1604592?tsid-17].
Lee, Hye J., "Protein Drug Oral Delivery: The Recent Progress" Archives of Pharmacal Research, 2002, vol. 25, No. 5, pp. 572-584.
Madsen, Kjeld et al., "Structure—Activity and Protraction Relationship of Long-Acting Glucagon-like Peptide-1 Derivatives: Importance of Fatty Acid Lenght, Polarity, and Bulkiness" J. Med. Chem., 2007, vol. 50, pp. 6126-6132.
Morishita, Mariko et al., "Is the oral route possible for peptide and protein drug delivery?" Drug Discovery Today, Oct. 2006, vol. 11, No. 19/20, pp. 905-910.
Novo Nordisk Company announcement No. 14/2015, Novo Nordisk announces positive results for phase 2 trial with oral semaglutide in people with type 2 diabetes, www.novonordisk.com CVR No. 24256790, dated Feb. 20, 2015, p. 1-2.
Novo Nordisk Company announcement No. 52/2015, Novo Nordisk to initiate phase 3a development of oral semaglutide, a once-daily oral GLP-1 analogue, www.novonordisk.com CVR No. 24256790, dated Aug. 26, 2015, p. 1-2.
Novo Nordisk Company announcement No. 17/2018, Novo Nordisk successfully completes the first phase 3a trial, PIONEER 1, with oral semaglutide, www.novonordisk.com CVR No. 24256790, dated Feb. 22, 2018, p. 1-3.
Novo Nordisk Company announcement No. 47/2018, Oral semaglutide shows superior improvement in HbA1C vs empagliflozin in the PIONEER 2 trial, www.novonordisk.com CVR No. 24256790, dated May 29, 2018, p. 1-3.
Novo Nordisk Company announcement No. 51/2018, Oral semaglutide shows statiistically significantly greater reductions in HbA1c and weight compared to Victoza® and sitagliptin in the PIONEER 4 and 7 trials, www. novonordisk.com CVR No. 24256790, dated Jun. 20, 2018, p. 1-4.
Novo Nordisk Company announcement No. 53/2018, Oral semaglutide shows superior reductions in HbA1c and weight compared to sitagliptin in the long-term safety and efficacy trial, PIONEER 3, www.novonordisk.com CVR No. 24256790, dated Jun. 28, 2018, p. 1-3.
Novo Nordisk Company announcement No. 66/2018, Oral semaglutide provides superior HbA1c and weight reductions versus placebo in people with type 2 diabetes and renal impairment in the PIONEER 5 trial, www.novonordisk.com CVR No. 24256790, dated Aug. 20, 2018, p. 1-3.
Novo Nordisk Company announcement No. 74/2018, Oral semaglutide demonstrates greater reductions in HbA1c and body weight and

(56) References Cited

OTHER PUBLICATIONS comparable number of adverse events vs dulaglutide in Japanese people with type 2 diabetes, www.novonordisk.com CVR No. 24256790, dated Sep. 20, 2018, p. 1-3.
Novo Nordisk Company announcement No. 81/2018, Oral semaglutide demonstrates statistically significant reductions in HbA1c and body weight in people with long duration of type 2 diabetes treated with insulin, www.novonordisk.com CVR No. 24256790, dated Oct. 26, 2018, p. 1-3.
Novo Nordisk Company announcement No. 89/2018, Oral semaglutide demonstrates greater reductions in both HbA1c and body weight compared to Victoza® in Japanese people with type 2 diabetes, www.novonordisk.com CVR No. 24256790, dated Nov. 22, 2018, p. 1-2.
Novo Nordisk Company announcement No. 90/2018, Oral semaglutide demonstrates a favourable cardiovascular safety profile and a significant reduction in cardiovascular death and all-casue mortality in people with type 2 diabetes in the PIONEER 6 trial, www.novonordisk.com CVR No. 24256790, dated Nov. 23, 2018, p. 1-3.
Owens, D. R. et al., "Alternative routes of insulin delivery" Diabetic Medicine, 2003, vol. 20, pp. 886-898.
Thepharmaletter, "'8-10 years ahead' of field in oral delivery, senior execs say Novo is becoming a GLP-1 company" May 16, 2018, [cited Jan. 24, 2019] Available from: [https://www.thepharmaletter.com/article/8-10-years-ahead-of-field-in-oral-delivery-senior-execs-say-novo-nordisk-is-becoming-a-glp-1-company].
Watson, Estelle et al., "Population Pharmacokinetics of Liraglutide, a Once-Daily Human Glucagon-Like Peptide-1 Analog, in Healthy Volunteers and Subjects With Type 2 Diabetes, and Comparison to Twice-Daily Exenatide" J. Clin Pharmacology, 2010, vol. 50, pp. 886-894.
Antony J Hickey et al., Pharmaceutical Process Engineering (Second edition) (2010) p. 155-168.
Bruce J. Aungst, "Absorption enhancers: applications and advances," The MPS Journal, 2011, vol. 14, No. 1, pp. 10-18.
Diabetes Close Up, Baby Steps, Mar./Apr. 2011, No. 106, pp. 1-50.
Dilip M. Parikh, Handbook of Pharmaceutical Granulation Technology (Second edition) (2005), Process-related variables, pp. 7-19 and 311-331.
EP Application 12160743, filed Mar. 22, 2012.
EP Application 13153459, filed Jan. 31, 2013.
Full European prosecution file of EP 2 827 885 BI. Published Jan. 28, 2015, Available at the EPO Register, https://register.epo.org/application?number=EP13709231 &lng=en&tab=doclist, accessed May 31, 2019.
Dilip M Parikh, Handbook of Pharmaceutical Granulation Technology, Drugs and pharmaceutical sciences, Second Edition, 2005, vol. 154, Introduction, pp. 1-6.
Post-published details of trial NCT01037582. First posted Dec. 23, 2009 https://clinicaltrials.gov/ct2/show/NCT01037582, accessed May 31, 2019.
Published details of trial NCT01037582 First Version Dec. 21, 2009 https://clinicaltrials.gov/ct2/history/NCT01037582?A=1&B=1&C=merged#StudyPageTop, accessed May 31, 2019.
R. F. Witkamp, "Current and Future Drug Targets in Weight Management," Pharm Res, 2011, vol. 28, pp. 1792-1818.
Salem et al., "Approaches to the pharmacological treatment of obesity," Expert Rev Clin Pharmacol, 2010, vol. 3, No. 1, pp. 73-88.
Barrera-Medrano et al., The Handbook of Powder Technology "Granulation", Chp. 25 granule structure, vol. 11, 2007, p. 1189-1212.
U.S. Appl. No. 61/748,840, filed Jan. 4, 2013.
Table summarizing the components of the tablet compositions B to F, described in EP Patent No. 2827885, issued Aug. 15, 2018.
Schematic drawing of tablets E and F described in EP Patent No. 2827885, issued Aug. 15, 2018.
Melanie Davies et al., "Effect of Oral Semaglutide Compared With Placebo and Subcutaneous Semaglutide on Glycemic Control in Patients With Type 2 Diabetes: A Randomized Clinical Trial," JAMA The Journal of the American Medical Association, 2017, vol. 318, No. 15, p. 1460.
Steinert et al., "Oral Administration of Glucagon-Like Peptide 1 or Peptide YY 3-36 Affects Food Intake in Healthy Male Subjects," Am J Clin Nutr, Oct. 2010, vol. 92, No. 4, pp. 810-817.
Full European prosecution file of EP 2 827 885 BI. Available at the EPO Register, https://register.epo.org/application?number=EP13709231 &lng=en&tab=doclist, accessed May 31, 2019.
Post-published details of trial NCT01037582 https://clinicaltrials.gov/ct2/show/NCT01037582, accessed May 31, 2019.
Published details of trial NCT01037582 (Dec. 2009) https://clinicaltrials.gov/ct2/history/NCT01037582?A=1&B=1&C=merged#StudyPageTop, accessed May 31, 2019.
Steinert et al., Oral administration of glucagon-like peptide 1 or peptide 3-36 affect food intake in healthy male subjects, "American Society for Nutrition", Am J Clin Nutr, 2010, vol. 92, pp. 810-817.
Nauck et al., 2012, Abstracts of the 48th European Association for the Study of Diabetes Annual Meeting of the EASD, Oct. 1-5, 2012, Berlin, Germany, Diabetologia, 2012, vol. 55, Suppl, S7.
Fonseca et al., "Efficacy and Safety of the Once-Daily GLP-1 Receptor Agonist Lixisenatide in Monotherapy," Diabetes Care, 2012, vol. 35, pp. 1225-1231.
Study NCT02014259, version 1, published Dec. 18, 2013, accessed Jun. 5, 2019.
"Drug Absorption, Distribution and Elimination; Pharmacokinetics" http://www.columbia.edu/itc/gsas/g9600/2004/GrazianoReadings/Drugabs.pdf, available since at least Apr. 24, 2006, accessed on Jun. 3, 2019.
Standards of Medical Care in Diabetes-2010, "Diabetes Care", vol. 33, supplement 1, Jan. 2010, pages S11-S61, care.diabetesjournals.org.
Andrew D. Morris, MD, "Addressing dosing frequency in diabetes: a simple approach to improving adherence to therapy and clinical outcomes," The Diabetes Educator, 2003, vol. 29, No. 3, pp. 440-453.
B.J. Aungst, "Absorption Enhancers: Applications and Advances," The AAPS Journal, 2012, vol. 14, No. 1, pp. 10-18.
ClinicalTrials.gov archive: History of Changes for Study NCT01686945, trackchange of version of Apr. 15, 2013 (published Apr. 16, 2013) as compared to version of Sep. 13, 2012 (published Sep. 18, 2012).
ClinicalTrials.gov archive: History of Changes for Study NCT01923181 (NN9924-3790).
Clinicaltrials.gov, NCT01686945, page as viewed in Apr. 2013, https://clinicaltrials.gov/ct2/history/NCT01686945?A=5&B=5&C=merged#Study PageTop.
Pechenov et al., "Development of an orally delivered GLP-1 receptor agonist through peptide engineering and drug delivery to treat chronic disease," Scientific Reports, Nov. 2021, vol. 11, No. 22521, pp. 1-15.
Wong et al., "Estimation of clinical trial success rates and related parameters," Biostatistics, Jan. 2018, vol. 20, No. 2, pp. 273-286.
Novo Nordisk Reply to Office Action dated Jul. 3, 2008 in EP1863839.
Gomez-Orella, "Strategies to Improve Oral Drug Bioavailability," Expert Opin Drug Deliv, 2005, vol. 2, No. 3: pp. 419-433.
Humphrey, M. J., "The Oral Bioavailability of Peptides and Related Drugs. In Delivery Systems for Peptide Drugs," Davis, S.S., Ilium, L., Tomlinson, E., Eds.; Springer Boston, MA, 1986; pp. 139-151.
Novo Nordisk's reply to the examination division dated Nov. 18, 2016 in EP Application 13729743.8, 3 pages.
Novo Nordisk's reply to the opposition grounds of WO2012/080471, corresponding to EP2651398, dated Feb. 15, 2019, 40 pages.
Kwan et al., "Factors Affecting Tablet Disintegration," Journal of the American Pharmaceutical Association, Scientific Edition, Apr. 1957, vol. XLVI, No. 4, pp. 236-239.
Viscasillas i Clerch, "Aportacion al diseno de un nuevo excipiente tipo "coprocessed product" para compresion directa," Universitat de Barcelona, 2008, pp. 159-160.
Pharmaceutical Binders and Their Function in Directly Compressed Tablets, Mechanistic Studies on the Effect of Dry Binders on Mechanical Strength, Pore Structure and Disintegration of Tablets, Dissertation for the Degree of Doctor of Philosophy (Faculty of

(56) References Cited

OTHER PUBLICATIONS

Pharmacy) in Pharmaceutics presented at Uppsala University in 2000 By Sofia Mattsson, pp. 32-34.
Extract of the opposed patent EP2863895, 2 pages, full prosecution file can be found in European Patent register https://register.epo.org/application?number=EP13729743&lng=en&tab=doclist.
File History of European Patent 2827845, filed Mar. 15, 2013.
File History of U.S. Appl. No. 61/662,456, filed Jun. 21, 2012.
Rowe et al., "Magnesium Stearate" and "Sodium Lauryl Sulfate", Handbook of Pharmaceutical Excipients, 6th Edition, 2009, pp. 404 407 and 651-653.
History of changes for clinical trial NCT01037582, from Mar. 17, 2011, https://clinicaltrials.gov/ct2/history/NCT01037582?A=5&C=merged#StudyPageTop.
Kikuta et al., "Effect of Mixing Time on the Lubricating Properties of Magnesium Stearate and the Final Characteristics of the Compressed Tablets," Drug Development and Industrial Pharmacy, 1994, vol. 20, No. 3, pp. 343-355.
Kusher IV et al., "Scale-up model describing the impact of lubrication on tablet tensile strength," International Journal of Pharmaceutics, vol. 399, Nos. 1-2, pp. 19-30.
Lieberman et al., Pharmaceutical Dosage Forms: Tablets, 2nd Edition, 1989, Chapter 5, pp. 247-284.
Parikh, Handbook of Pharmaceutical Granulation Technology, 3rd Edition, 2010, Informa Healthcare, pp. 2-3.
Remington, The Science and Practice of Pharmacy, 21st Edition, 2005, Lippincott, Williams & Wilkins, pp. 677, 892-893, 896, and 1040.
Sakr et al., "Oral Solid Dosage Forms," Remington, Essentials of Pharmaceutics, 1st Edition, Chapter 30, pp. 581-610.
Valtrex 500mg Tablets—Summary of Product Characteristics (SmPC), Sep. 26, 2019, pp. 1-10.
Teng et al., "Systematical approach of formulation and process development using roller compaction," European Journal of Pharmaceutics and Biopharmaceutics, 2009, vol. 73, pp. 219-229.
Parikh, "Drugs and the Pharmaceutical Sciences", Handbook of Pharmaceutical Granulation Technology, 2010, Third Edition, vol. 198, Chapter 2 Theory of Granulation: An Engineering Perspective, Chapter 8 Roller Compaction Technology and Chapter 9 Wes Granulation in Low- and high-Shear Mixers.
Uros Markoja, Semaglutide-Experiment report for opposition against EP2827845B1, dated Sep. 24, 2019, pp. 1-6.
Valtrex prescribing information (valacyclovir hydrochloride caplets), GlaxoSmithKline, Oct. 2007, pp. 1-20.
Venables et al., "Powder Mixing," Drug Development and Industrial Pharmacy, 2001, vol. 27, No. 7, pp. 599-612.
Tyagi et al., "Oral peptide delivery: Translational challenges due to physiological effects," J. Controlled Release, 2018, vol. 287, pp. 167-176.
Dahlgren et al., "Intestinal absorption-modifying excipients: A current update on preclinical in vivo evaluations," European J. of Pharm. and Biopharmaceutics, 2019, vol. 142, pp. 411-420.
Figures presenting plasma concentration, described in EU Patent No. 2991671, issued Aug. 15, 2018.
FDA News Release, "FDA approved first oral GLP-1 treatment for type 2 diabetes," Sep. 20, 2019.
Carly Helfand, "Novo Nordisk wins FDA green light for "holy grail" diabetes drug Rybelsus," Fierce Pharma, Sep. 20, 2019, https://www.fiercepharma.com/pharma/novo-nordisk-wins-fda-green-light-for-holy-grail-oral-semaglutide, accessed Oct. 4, 2019.
Runge et al., "Crystal Structure of the Ligand-Bound Glucagon-Like Peptide-1 Receptor Extracellular Domain," J Biol Chem 2008, vol. 283, No. 17, pp. 11340-11347.
Adelhorst, K et al Journal of Biological Chemistry Structure Activity Studies of GLP-1 1994 2699 6275-6278.
Knudsen, L.B. Journal of Medicinal Chemistry Glucagon-Like Peptide-1: the Basis of a New Class of Treatment for Type 2 Diabetes 2004 47 17 4128-4134.

Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan et al., Design of a Long Acting Peptide Functioning as both a Glucagon-like Peptide-1 Receptor Agonist and a Glucagon Receptor Antagnist, "The Journal of Biological Chemistry", May 2006, vol. 281, No. 18, pp. 12506-12515.
The Medical Dictionary Online. http://cancerweb.ncl.ac.uklomd/about.html. 2005.
Nauck, M A. Regulatory Peptides. "Glucagon-Like Peptide 1 and its Derivatives in the Treatment od Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.
Overview of claim 1 of the main and auxiliary requests, European Application No. EP2651398, filed May 14, 2013.
GenScript, "Peptide YY (PYY) (3-36), human," https://www.genscript.com/peptide/RP10354-Peptide_YY_PYY_3_36_human.html, accessed Jan. 27, 2020.
Banakar et al, Critical Considerations in Pharmaceutical Bioequivalence Testing, Journal of Pharmacy of University of Marmara, 1995, vol. 11 Nos. 1-2, pp. 55-80.
Emisphere Technologies, Inc., Form 10-K, 2013 Annual Report, Published Mar. 31, 2014.
American Veterinary Medical Association, "The Veterinarian-Client-Patient Relationship (VCPR)," https://www.avma.org/policies/veterinarian-client-patient-relationship, accessed Mar. 11, 2020.
National Institute of Diabetes and Digestive and Kidney Diseases,"Prescription Medications to Treat Overweight and Obesity," Jul. 2016, 10 pages, retrieved on Apr. 13, 2020, URL: https://www.niddk.nih.gov/health-information/weight-management/prescription-medications-treat-overweight-obesity.
W.K. Sietsema, "The absolute oral bioavailability of selected drugs." Mar. 1989, International Journal of Clinical Pharmacology, Therapy and Toxicology, vol. 27, No. 4, pp. 179-211.
Declaration of Doctor Peter Rue, for EP2827885 dated Jul. 29, 2020.
Declaration of Professor Leon Aarons for EP2827885 dated Jul. 29, 2020.
Shajahan et al., A flexible technology for modified-release drugs: Multiple-unit pellet system (MUPS) May 2009, Journal of Controlled Release, vol. 147, No. 1, pp. 2-16.
Physicians' Desk Reference, 54th Edition, 2000, p. 1291.
Physicians' Desk Reference, 63rd Edition, 2009, p. 1638.
Anne Mari Juppo, "Porosity parameters of lactose, glucose and mannitol tablets obtained by mercury porosimetry," International Journal of Pharmaceutics, 1996, vol. 129, pp. 1-12.
Michael E. Aulton, "Aulton's Pharmaceutics. The design and manufacture of medicines" Churchill Livingstone Elsevier, 2007, Ed. 3rd, Chapter 21, pp. 286-303.
Linda Felton, "Remington Essentials of Pharmaceutics," Pharmaceutical Press, 2012, Chapter 6, pp. 63-80 and Chapter 30, pp. 581-610.
Qiu et al., "Developing Solid Oral Dosage Forms" Pharmaceutical Theory and Practice, Academic Press, 2009, 1st Edition, pp. 175-186.
James Swarbrick, "Encyclopedia of Pharmaceutical Technology. vol. 1," Informa Healthcare USA, Inc., 2007, Ed. 3rd, pp. 164-175 and 988-1000.
EP application No. 12160743.6, filed Mar. 22, 2012.
Betts et al., Chapter 14, "Amino Acid Properties and Consequences of Substitutions," Bioinformatics for Geneticists (2003) ed. By Barnes and Gray, John Wiley & Sons, Ltd., pp. 289-316.
Kojima S et al. A role for pancreatic polypeptide in feeding and body weight regulation, "Peptides", Year 2007, vol. 28, No. 2, pp. 459 463.
Lin Shu et al. Critical Role of Arcuate Y4 Receptors and the Melanocortin System in Pancreatic Polypeptide-Induced Reduction in Food Intake in Mice, "PLOS ONE" Year 2009, vol. 4, No. 12, pp. e8488-e8488.

(56) References Cited

OTHER PUBLICATIONS

Ito T et al, Effects of peripheral administration of PYY3-36 on feed intake and; plasma acyl-ghrelin levels in pigs, Journal of Endocrinology, Year 2006, vol. 191, pp. 113-119.
Ortiz A. et al, A Novel Long-Acting Selective Neuropeptide Y2 Receptor Polyethylene Glycol-Conjugated Peptide Agonist Reduces Food Intake and Body Weight and Improves Glucose Metabolism in Rodents , The Journal of Pharmacology and Experimental Therapeutics (2007), vol. 323, No. 2, pp. 692-700.
Roger Reidelberger et al., Effects of Glycine-Extended and Serine13-Phosphorylated Forms of Peptide YY on Food Intake in Rats, Peptides, Year 2011; vol. 32, No. 4, pp. 770-775.
Søren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.
Van den Hoek A. et al., Chronic PYY3-36 treatment promotes fat oxidation and ameliorates insulin resistance in C57BL6 mice, American Journal of Physiology-Endocrinology and Metabolism, Year 2007, 292, pp. E238-E245.
Adrian et al., Gut, 1978, vol. 19, No. 10, pp. 907-909.
Heizmann et al., Peptide Research, "Synthesis of an N-3-guanidinopropylglycine (Narg) Derivative as a Versatile Building Block for Solid-Phase Peptide and Peptoid Synthesis", 1994, vol. 7, No. 6, pp. 328-332.
Batterham, R.L. et al., "Gut Hormone PYY3-36 Physiologically Inhibits Food Intake", Nature, 2002, vol. 418, pp. 650-654.
Bowie et al. (Science, 1990, 247:1306-1310).
Burgess et al. (J. Cell Biol. 111:2129-2138, 1990).
Lazar et al. (Mol. Cel. Biol., 8:1247-1252, 1988).
Bork (Genome Research, 2000, 10:398-400).
T.W. Schwartz., "Pancreatic Polypeptide: A Hormone Under Vagal Control", Gastroenterology. 1983, vol. 85, pp. 1411-1425.
Whitcomb. Am. J. Physiol. "Characterization of saturable binding sites for circulating pancreatic polypeptide in rat brain." 1990 vol. 259 G687-G691.
Jorgensen, J. Ch. et al. Euro. J. Pharmacol. "Structure-function studies on neuropeptide Y and pancreatic polypeptide-evidence for two PP-fold receptors in vas deferens" 1990 vol. 186: 105-114.
Cooke, D et al. Nature Reviews. "The obesity pipeline: current strategies in the development of anti-obesity drugs" 2006 vol. 5: 919-930.
Kamiji, M.M et al. Current Topics in Medical Chemistry "NPY Y2 and Y4 receptors selective ligands: promising anti-obesity drugs?" 3008 vol. 7: 1734-1742.
Sainsbury, A. et al. Mol Nad Cell Biol "Synergistic Effects of Y2 and Y4 Receptors on Adiposity and Bone Mass Revealed in Double Knockout Mice" vol. 23: 5225-5233.
Sampson, W.R. J. Pep. Sci. "The Synthesis of 'Difficult' Peptides Using 2-Hydroxy-4-Methoxybenzyl or Pseudoproline Amino Acid Building Blocks: a Comparative Study" 1999 vol. 5: 403.
Knudsen et al. J Med Chem. "Potent Derivatives of Glucagon-Like Peptide-1 with Pharmacokinetic Properties Suitable for Once Daily Administration" 2000. vol. 43(9). p. 1664-1669.
Boggiano, M.M. et al, "PYY3-36 as an anti-obesity drug target", Obesity Reviews. 2005 vol. 6: 307-322.
Dodson, Shontelle et al "Muscle Wasting in Cancer Cachexia: Clinical Implications, Diagnosis, and Emerging Treatment Strategies" Annu. Rev. Med. 2011 vol. 62 pp. 265-279.
Muscaritoli, Maurizio et al "Prevention and Treatment of Cancer Cachexia: New Insights into an Old Problem." European Journal of Cancer, 2006 vol. 42 pp. 31-41.
Soeren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.
Van den Hoek A. et al., Chronic PYY3-36 treatment promotes fat oxidation and ameliorates insulin resistance in C57BL6 mice, American Journal of Physiology-Endocrinology and Metabolism, Year 2007, vol. 292, No. 1 pp. E238-E245.

Kouki Kitagawa et al: Solution synthesis of human peptide YY(hPYY),Chemical & Pharmaceutical Bulletin,Year Jun. 1, 1990 vol. 38, No. 6, pp. 1731-1734.
Ortiz A. et a lA Novel Long-Acting Selective Neuropeptide Y2 Receptor Polyethylene Glycol-Conjugated Peptide Agonist Reduces Food Intake and Body Weight and Improves Glucose Metabolism in Rodents, The Journal of Pharmacology and Experimental Therapeutics Year 2007, vol. 323 No. 2, pp. 692-700.
Roger Reidelberger et al: "Effects of glycine-extended and serine-phosphorylated forms of peptide YY on food intake in rats", Peptides,Peptides Year 2011,vol. 32, No. 4, pp. 770-775.
Van den Hoek A. et al. Chronic PYY3-36 treatment promotes fat oxidation and ameliorates insulin resistance in C57BL6 mice American Journal of Physiological Endocrinology and Metabolism Year 2006,vol. 292, No. 1 pp. E238-E245.
Balasubramaniam et al., "Structure-Activity Studies Including a psi(CH2-NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, vol. 43, pp. 3420-3427.
Atherosclerosis, from http://www.merckmanuals.com/professional/cardiovascular-disorders/arteriosclerosis/atherosclerosis, pp. 1-14, accessed Dec. 29, 2015.
Diabetes, from http://www.merckmanuals.com/professional/endocrine-and-metabolic-disorders/ . . . , pp. 1-34, accessed Sep. 2, 2016.
Dyslipidemia, from http://www.merckmanuals.com/professional/endocrine-and-metabolic-disorders/lipid-dis . . . , pp. 1-11, accessed Dec. 29, 2015.
Fatty Liver Disease, from http://www.webmd.com/hepatitis/fatty-liver-disease?page=2&print=true, pp. 1-4, accessed Dec. 29, 2015.
Nabel, "Cardiovascular Disease," New Engl. J. Med., 2003, vol. 349, pp. 60-72.
Neary et al., "Peptide YY: Food for thought," Physiology & Behavior 97: 616-619 (2009).
Nonatheromatous Arteriosclerosis, from http://www.merckmanuals.com/professional/cardiovascular-disorders/arteriosclerosis/non . . . , pp. 1-2, accessed Dec. 29, 2015.
Sam et al., "Selective Ablation of Peptide YY Cells in Adult Mice Reveals Their Role in Beta Cell Survival," Gastroenterology, 143:459-468 (2012).
Vincent et al., "The satiety hormone peptide YY as a regulator of appetite," J Clin Pathol 61 :548-552 (2008).
Zhao Na et al., "PYY and obesity (summary)," Sports and Research Education, 2012, vol. 27, No. 3, pp. 102-107.
Huang Lan et al., "Relationship between Peptide Tyrosine-Tyrosine 3-36 and Ingestion Regulation," Hubei Agriculture Sciences, 2009, vol. 48, No. 10, pp. 2591-2594.
Zhao Biqian et al., "Regulation of PYY on Animal Food Intakes," Feed Industry, 2010, vol. 31, No. 18, pp. 51-55.
Beglinger et al. "Pharmacokinetics and pharmacodynamic effects of oral GLP?1 and PYY3?36: a proof?of?concept study in healthy subjects." Clinical Pharmacology & Therapeutics, Oct. 2008, vol. 84, No. 4, pp. 468-474.
Schmidt et al.,"Effects of PYY3-36 and GLP-1 on energy intake, energy expenditure, and appetite in overweight men." American Journal of Physiology—Endocrinology and Metabolism, Apr. 2014, vol. 306, No. 11. pp. E1248-E1256.
Steinert et al.,"Oral administration of glucagon-like peptide 1 or peptide YY 3-36 affects food intake in healthy male subjects." The American journal of clinical nutrition, Oct. 2010, vol. 92, No. 4, p. 810-817.
Cox Gad, Shayne, "Pharmaceutical Manufacturing Handbook Production and Processes," Hoboken, New Jersey Wiley-Interscience A John Wiley & Sons, Inc., 2008, pp. 235-265 and 881-1222.
Hancock et al., "The Relative Densities of Pharmaceutical Powders, Blends, Dry Granulations, and Immediate-Release Tablets," Pharmaceutical Technology, Apr. 2003, p. 64-80.
Hoffman et al., "Eligen insulin—a system for the oral delivery of insulin for diabetes," IDrugs, 2008, vol. 11, pp. 433-441.
Lowenthal, Werner, "Disintegration of Tablets" Journal of Pharmaceutical Sciences, Nov. 1972, vol. 61, No. 11, pp. 1695-1711.

(56) References Cited

OTHER PUBLICATIONS

Poole, John W., "Effects of Formulation and Dosage Form on Drug Bioavailability" Principles and Perspectives in Drug Bioavailability, Chapters, Karger, 1979, pp. 59-89.
Rudnic et al., "Oral Solid Dosage Forms," Chapter 45, Remington—The Science and Practice of Pharmacy, Philadelphia, PA: Lippincott Williams & Wilkins, 2006, Ed. 21st, pp. 889-927.
Tong, W.Q., "Molecular and Physicochemical Properties Impacting Oral Absorption of Drugs" Biopharmaceutics Applications in Drug Development, Chapter 2, Springer, 2008, pp. 26-46.
Study protocol of trial NCT01037582 of Dec. 2009, 7 pages.

* cited by examiner

SEQUENCE LISTING

<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40
<212> TYPE: PRT
<213> ORGANISM: Heloderma suspectum

<400> SEQUENCE: 2

His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

```
Ser Ser Gly Ala Pro Pro Pro Ser
    35              40
```

SOLID COMPOSITIONS COMPRISING A GLP-1 AGONIST AND A SALT OF N-(8-(2-HYDROXYBENZOYL)AMINO)CAPRYLIC ACID

CROSS-REFERENCE TO RELATED APPLICATIONS

This application is a continuation of U.S. application Ser. No. 16/118,381, filed Aug. 30, 2018, which is a continuation of U.S. application Ser. No. 15/019,412, filed Feb. 9, 2016 (Issued as U.S. Pat. No. 10,086,047), which is a continuation of U.S. application Ser. No. 13/994,262 filed Sep. 16, 2013 (Issued as U.S. Pat. No. 9,278,123), which is a 35 U.S.C. § 371 National Stage application of International Application PCT/EP2011/073060 (WO 2012/080471), filed Dec. 16, 2011, which claimed priority of European Patent Application 10195285.1, filed Dec. 16, 2010; this application claims priority under 35 U.S.C. § 119 of U.S. Provisional Application 61/425,087; filed Dec. 20, 2010; the contents of which are incorporated herein by reference.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Feb. 19, 2021, is named 8253US05_SequenceListing_ST25.txt and is 2 kilobytes in size.

FIELD OF THE INVENTION

The present invention relates to solid compositions comprising a GLP-1 agonist and a salt of N-(8-(2-hydroxybenzoyl)amino)caprylic acid and their use in medicine.

BACKGROUND OF THE INVENTION

Human GLP-1 and analogues thereof have a low oral bioavailability. Exposure and bioavailability of human GLP-1 and analogues thereof is very low following oral administration. Human GLP-1 and analogues thereof can only be detected in plasma after oral administration if formulated with certain absorption enhancers in a specific amount. Steinert et al. (Am J Clin Nutr, October 2010; 92: 810-817) discloses oral administration of a tablet comprising GLP-1(7-36)amide and 150 mg sodium N-(8-(2-hydroxybenzoyl)amino)caprylate (SNAC). WO 2010/020978 discloses an oral pharmaceutical composition comprising a protein and N-(8-[2-hydroxybenzoyl)amino)caprylate (SNAC).

There is still a need for an optimized pharmaceutical composition for oral administration of a GLP-1 agonist such as a GLP-1 agonist comprising a substituent.

SUMMARY OF THE INVENTION

In some embodiments the invention relates to a solid composition for oral administration comprising a GLP-1 agonist and a salt of N-(8-(2-hydroxybenzoyl)amino) caprylic acid, wherein a) the amount of said salt of N-(8-(2-hydroxybenzoyl)amino) caprylic acid is at least 0.6 mmol or at least 0.8 mmol; and b) said GLP-1 agonist is GLP-1 (7-37), GLP-1 (7-36)amide, exendin-4 or an analogue thereof, and wherein said GLP-1 agonist optionally comprises one substituent. In some embodiments the invention relates to the use of a composition as defined herein in medicine.

DESCRIPTION OF THE INVENTION

The present invention relates to solid compositions of a GLP-1 agonist and salt of N-(8-(2-hydroxybenzoyl)amino) caprylic acid. Surprisingly, the present inventors have found that solid compositions comprising certain amounts of a salt of N-(8-(2-hydroxybenzoyl)amino)caprylic acid, such as SNAC, are optimal for oral administration of GLP-1 agonists. Accordingly, the compositions provide improved exposure and/or bioavailability of the GLP-1 agonist.

Generally, the term "bioavailability" as used herein refers to the fraction of an administered dose of an active pharmaceutical ingredient (API), such as a GLP-1 agonist as defined herein, which reaches the systemic circulation unchanged. By definition, when an API is administered intravenously, its bioavailability is 100%. However, when it is administered via other routes (such as orally), its bioavailability decreases (due to incomplete absorption and first-pass metabolism). Knowledge about bioavailability is important when calculating dosages for non-intravenous routes of administration.

Absolute oral bioavailability is calculated as the relative exposure of the API in systemic circulation following oral administration (estimated as the area under the plasma concentration versus time curve, or AUC) compared to the exposure of the API following intravenous administration.

GLP-1 Agonist

The term "GLP-1 agonist" as used herein refers to a compound, which fully or partially activates the human GLP-1 receptor. In some embodiments the "GLP-1 agonist" binds to a GLP-1 receptor, e.g., with an affinity constant ($K_D$) or activate the receptor with a potency ($EC_{50}$) of below 1 µM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 agonist may be administered to an animal with increased blood glucose (e.g. obtained using an Intravenous Glucose Tolerance Test (IVGTT), a person skilled in the art will be able to determine a suitable glucose dosage and a suitable blood sampling regime, e.g. depending on the species of the animal, for the IVGTT) and the plasma insulin concentration measured over time.

In some embodiments the GLP-1 agonist is a GLP-1 analogue, optionally comprising one substituent. The term "analogue" as used herein referring to a GLP-1 peptide (hereafter "peptide") means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition or deletion of amino acid residues may take place at the N-terminal of the peptide and/or at the C-terminal of the peptide. In some embodiments a simple nomenclature is used to describe the GLP-1 agonist, e.g., [Aib8] GLP-1(7-37) designates an analogue of GLP-1(7-37) wherein the naturally occurring Ala in position 8 has been substituted with Aib. In some embodiments the GLP-1 agonist comprises a maximum of twelve, such as a maximum of 10, 8 or 6, amino acids which have been alterered, e.g., by substitution, deletion, insertion and/or modification, compared to e.g. GLP-1(7-37). In some embodiments the analogue comprises up to 10 substitutions, deletions, additions and/or insertions, such as up to 9 substitutions, deletions, additions and/or insertions, up to 8 substitutions, deletions, additions and/or insertions, up to 7 substitutions, deletions, additions and/or insertions, up to 6 substitutions, deletions, additions and/or insertions, up to 5 substitutions, deletions, additions and/or insertions, up to 4 substitutions, deletions, additions and/or insertions or up to 3 substitutions, deletions, additions and/or insertions, compared to e.g. GLP-1(7-37). Unless otherwise stated the GLP-1 comprises only L-amino acids.

In some embodiments the term "GLP-1 analogue" or "analogue of GLP-1" as used herein refers to a peptide, or a compound, which is a variant of the human Glucagon-Like Peptide-1 (GLP-1(7-37)). GLP-1(7-37) has the sequence HAEGTFTSDV SSYLEGQAAKEFIAWLVKGRG (SEQ ID No: 1). In some embodiments the term "variant" refers to a compound which comprises one or more amino acid substitutions, deletions, additions and/or insertions.

In one embodiment the GLP-1 agonist exhibits at least 60%, 65%, 70%, 80% or 90% sequence identity to GLP-1 (7-37) over the entire length of GLP-1(7-37). As an example of a method for determination of sequence identity between two analogues the two peptides [Aib8]GLP-1(7-37) and GLP-1(7-37) are aligned. The sequence identity of [Aib8] GLP-1(7-37) relative to GLP-1(7-37) is given by the number of aligned identical residues minus the number of different residues divided by the total number of residues in GLP-1 (7-37). Accordingly, in said example the sequence identity is (31-1)/31.

In one embodiment the C-terminal of the GLP-1 agonist is an amide.

In some embodiments the GLP-1 agonist is GLP-1(7-37) or GLP-1(7-36)amide. In some embodiments the GLP-1 agonist is exendin-4, the sequence of which is HGEGT-FITSDLSKQMEEEAVRLFIEWLKNGGPSSGAPPPS (SEQ ID No: 2).

In some embodiments the GLP-1 agonist comprises one substituent which is covalently attached to the peptide. In some embodiments the substituent comprises a fatty acid or a fatty diacid. In some embodiments the substituent comprises a C16, C18 or C20 fatty acid. In some embodiments the substituent comprises a C16, C18 or C20 fatty diacid. In some embodiments the substituent comprises formula (X)

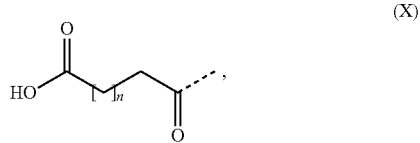

(X)

wherein n is at least 13, such as n is 13, 14, 15, 16, 17, 18 or 19. In some embodiments the substituent comprises formula (X), wherein n is in the range of 13 to 19, such as in the range of 13 to 17. In some embodiments the substituent comprises formula (X), wherein n is 13, 15 or 17. In some embodiments the substituent comprises formula (X), wherein n is 13. In some embodiments the substituent comprises formula (X), wherein n is 15. In some embodiments the substituent comprises formula (X), wherein n is 17. In some embodiments the substituent comprises one or more 8-amino-3,6-dioxaoctanoic acid (OEG), such as two OEG.

In some embodiments the substituent is [2-(2-{2-[2-(2-{2-[(S)-4-carboxy-4-(17-carboxyheptadecanoylamino) butyrylamino]ethoxy}ethoxy)acetylamino] ethoxy}ethoxy) acetyl].

In some embodiments the substituent is [2-(2-{2-[2-(2-{2-[(S)-4-carboxy-4-({trans-4-[(19-carboxynonadecanoy-lamino)methyl]cyclohexanecarbonyl} amino)butyrylamino] ethoxy}ethoxy)acetylamino]ethoxy}ethoxy)acetyl].

In some embodiments the GLP-1 agonist is semaglutide, also known as N-epsilon26-[2-(2-{2-[2-(2-{2-[(S)-4-carboxy-4-(17-carboxyheptadecanoylamino) butyrylamino] ethoxy}ethoxy)acetylamino]ethoxy}ethoxy)acetyl][Aib8, Arg34]GLP-1(7-37), which may be prepared as described in WO2006/097537, Example 4.

In some embodiments the composition comprises the GLP-1 agonist or a pharmaceutically acceptable salt, amide, or ester thereof. In some embodiments the composition comprises the GLP-1 agonist one or more pharmaceutically acceptable counter ions.

In some embodiments the dosage of GLP-1 is in the range of 0.01 mg to 100 mg. In some embodiments the composition comprises an amount of a GLP-1 agonist in the range of 0.1 to 40 mg or 1 to 20 mg. In some embodiments the composition comprises an amount of a GLP-1 agonist in the range of 5 to 20 mg, such as in the range of 5 to 15 mg, such as 5 mg, such as 10 mg, such as 15 mg, such as 20 mg.

In some embodiments the composition comprises an amount of a GLP-1 agonist in the range of 0.05 to 25 µmol, such as in the range of 0.5 to 2.5 µmol.

In some embodiments the GLP-1 agonist is selected from one or more of the GLP-1 agonists mentioned in WO93/19175, WO96/29342, WO98/08871, WO99/43707, WO99/43706, WO99/43341, WO99/43708, WO2005/027978, WO2005/058954, WO2005/058958, WO2006/005667, WO2006/037810, WO2006/037811, WO2006/097537, WO2006/097538, WO2008/023050, WO2009/030738, WO2009/030771 and WO2009/030774.

In some embodiments the GLP-1 agonist is selected from the group consisting of N-epsilon37{2-[2-(2-{2-[2-((R)-3-carboxy-3-{[1-(19-carboxynonadecanoyl) piperidine-4-carbonyl]amino}propionylamino)ethoxy]ethoxy}acetylamino) ethoxy]ethoxy}acetyl [desaminoHis7,Glu22,Arg26,Arg34, Lys37]GLP-1(7-37)amide; N-epsilon26{2-[2-(2-{2-[2-((R)-3-carboxy-3-{[1-(19-carboxynonadecanoyl) piperidine-4-carbonyl]amino} propionylamino)ethoxy] ethoxy}acetylamino)ethoxy] ethoxy}acetyl [desaminoHis7, Arg34] GLP-1-(7-37); N-epsilon37{2-[2-(2-{2-[2-((S)-3-carboxy-3-{[1-(19-carboxy-nonadecanoyl) piperidine-4-carbonyl]amino}propionylamino)ethoxy] ethoxy} acety-lamino)ethoxy] ethoxy}acetyl[Aib8,Glu22,Arg26,Arg34, Lys37]GLP-1-(7-37)amide; N-epsilon37-[2-(2-[2-(2-[2-(2-((R)-3-[1-(17-carboxyheptadecanoyl)piperidin-4-ylcarbonylamino]3-carboxypropionylamino)ethoxy)ethoxy] acetylamino)ethoxy] ethoxy)acetyl][,DesaminoHis7, Glu22 Arg26, Arg 34, Phe(m-CF3)28]GLP-1-(7-37)amide; N-epsilon26-[(S)-4-carboxy-4-({trans-4-[(19-carboxynonade-canoylamino)methyl] cyclohexanecarbonyl}amino)butyryl] [Aib8,Arg34]GLP-1-(7-37); N-epsilon26-{4-[(S)-4-carboxy-4-({trans-4-[(19-carboxynonadecanoylamino) methyl]cyclohexanecarbonyl} amino)butyrylamino]butyryl}[Aib8,Arg34]GLP-1-(7-37); N-epsilon26-[2-(2-{2-[(S)-4-carboxy-4-({trans-4-[(19-carboxy-nonadecanoy-lamino) methyl]cyclohexanecarbonyl} amino) butyrylamino]ethoxy}ethoxy)acetyl][Aib8,Arg34]GLP-1-(7-37); N-epsilon26-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy)

acetylamino]ethoxy}ethoxy) acetyl][Aib8,Arg34]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino) butyrylamino]ethoxy}ethoxy)acetylamino]ethoxy}ethoxy)acetyl][Aib8,Glu22,Arg26, Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino) butyrylamino]ethoxy}ethoxy)acetylamino]ethoxy}ethoxy)acetyl][DesaminoHis7,Glu22, Arg26,Arg34,Lys37]GLP-1-(7-37)amide; N-epsilon37-[2-(2-{2-[2-(2-{2-[(S)-4-carboxy-4-({4-[(trans-19-carboxy-nonadecanoylamino)methyl]cyclohexanecarbonyl}amino) butyrylamino]ethoxy}ethoxy)acetylamino]ethoxy}ethoxy)acetyl][DesaminoHis7,Arg26, Arg34,Lys 37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino) butyrylamino]ethoxy}ethoxy)acetylamino]ethoxy}ethoxy)acetyl][DesaminoHis7,Glu22,Arg26,Arg 34,Lys37]GLP-1-(7-37); N-epsilon26[2-(2-{2-[2-(2-{2-[(S)-4-carboxy-4-({4-[(19-carboxy-nonadecanoylamino)methyl]cyclohexanecarbonyl}amino)butyrylamino] ethoxy}ethoxy)acetylamino]ethoxy}ethoxy)acetyl[Aib8, Lys 26]GLP-1 (7-37)amide; N-epsilon26 [2-(2-{2-(2-[2-(2-((S)-2-[trans-4-((9-carboxynonadecanoylamino] methyl) cyclohexylcarbonylamino]-4-carboxybutanoylamino)ethoxy)ethoxy]acetylamino) ethoxy]ethoxy)acetyl][Aib8, Lys26] GLP-1 (7-37) amide; N-epsilon37-[2-(2-{2-[2-(2-{2-[(S)-4-carboxy-4-({trans-4-[(19-carboxy-nonadecanoylamino)methyl]cyclohexanecarbonyl} amino)butyrylamino]ethoxy}ethoxy)acetylamino]ethoxy}ethoxy)acetyl] [DesaminoHis7,Arg26, Arg34,Lys37]GLP-1-(7-37); N-epsilon37-[2-(2-{2-[2-(2-{2-[(S)-4-carboxy-4-({trans-4-[(19-carboxy-nonadecanoylamino)methyl]cyclohexanecarbonyl} amino) butyrylamino]ethoxy}ethoxy)acetylamino]ethoxy}ethoxy)acetyl][DesaminoHis7,Glu2 2,Arg26,Glu30,Arg34,Lys37]GLP-1-(7-37); N-epsilon26-[2-(2-{2-[(S)-4-carboxy-4-((S)-4-carboxy-4-{4-[4-(16-(1H-tetrazol-5-yl)-hexadecanoylsulfamoyl)butyrylamino]-butyrylamino}butyrylamino) butyrylamino] ethoxy}ethoxy)acetyl][Aib8,Arg34]GLP-1-(7-37); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyrylamino) butyrylamino] ethoxy}ethoxy)acetyl][Aib8,Arg34]GLP-1-(7-37); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino} butyrylamino)butyrylamino] ethoxy}ethoxy) acetyl][Aib8,Arg34]GLP-1-(7-37); N-epsilon26-[2-(2-{2-[(S)-4-carboxy-4-((S)-4-carboxy-4-{4-[4-(16-(1H-tetrazol-5-yl)hexadecanoylsulfamoyl)butyrylamino] butyrylamino}butyrylamino)butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]-dodecanoylamino}butyrylamino) butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino) butyrylamino]ethoxy}ethoxy)acetyl] [Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyrylamino)butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino} butyrylamino)butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino) butyrylamino]ethoxy}ethoxy)acetyl][Aib8,Arg34]GLP-1-(7-36)amide; N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyryl-amino)butyrylamino]ethoxy} ethoxy)acetyl][Aib8,Lys33,Arg34]GLP-1-(7-34); N-epsilon26-[2-(2-{2-[(S)-4-carboxy-4-((S)-4-carboxy-4-{12-[4-(16-(1H-tetrazol-5-yl) hexadecanoylsulfamoyl)butyrylamino] dodecanoylamino}butyrylamino)butyrylamino] ethoxy}ethoxy)acetyl][Aib8,Arg34]GLP-1-(7-36)amide; N-epsilon26-[2-(2-{2-[2-(2-{2-[2-(2-{2-[2-(2-{2-[2-(2-{2-[(S)-4-carboxy-4-((S)-4-carboxy-4-{12-[4-(16-(1H-tetrazol-5-yl)hexadecanoylsulfamoyl) butyrylamino] dodecanoylamino}butyrylamino) butyrylamino] ethoxy}ethoxy) acetylamino]ethoxy}ethoxy)acetylamino] ethoxy}ethoxy)acetylamino]ethoxy}ethoxy)acetylamino] ethoxy}ethoxy)acetylamino]ethoxy}ethoxy)acetyl][Aib8, Lys26,Arg34]GLP-1-(7-36)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino] dodecanoylamino}butyrylamino) butyrylamino] ethoxy}ethoxy)acetyl][Aib8,Glu22,Arg26,Arg34,Lys37] GLP-1-(7-37)amide; N-epsilon37-[2-(2-{2-[(S)-4-carboxy-4-((S)-4-carboxy-4-{12-[4-(16-(1H-tetrazol-5-yl) hexadecanoylsulfamoyl)butyrylamino] dodecanoylamino}butyrylamino) butyrylamino] ethoxy}ethoxy)acetyl][DesaminoHis7,Glu22,Arg26,Arg34,Lys37]GLP-1-(7-37)amide; N-epsilon37{2-[2-(2-{2-[2-((R)-3-carboxy-3-{[1-(19-carboxy-nonadecanoyl) piperidine-4-carbonyl]amino}propionylamino)ethoxy]ethoxy}acetylamino)ethoxy] ethoxy}acetyl [desaminoHis7,G1u22,Arg26,Arg34,Lys37]GLP-1(7-37)amide; N-epsilon37{2-[2-(2-{2-[2-((S)-3-carboxy-3-{[1-(19-carboxynonadecanoyl) piperidine-4-carbonyl]amino} propionylamino) ethoxy] ethoxy}acetylamino)ethoxy} ethoxy} acetyl [Aib8,Glu22, Arg26,Arg34, Lys37]GLP-1-(7-37)amide; N-epsilon37-[2-(2-[2-[2-(2-((R)-3-[1-(17-carboxyhepta-decanoyl)piperidin-4-ylcarbonylamino]3-carboxy-propionylamino) ethoxy) ethoxy] acetylamino) ethoxy] ethoxy)acetyl] [DesaminoHis7, Glu22,Arg26, Arg34,Phe(m-CF3)28] GLP-1-(7-37)amide; N-epsilon37-[2-(2-{2-[2-(2-{2-[(S)-4-carboxy-4-({trans-4-[(19-carboxy-nonadecanoylamino) methyl] cyclohexanecarbonyl} amino)butyrylamino] ethoxy} ethoxy)acetylamino] ethoxy}ethoxy)acetyl] [Aib8, Glu22,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl} amino)butyrylamino]ethoxy}ethoxy) acetylamino] ethoxy}ethoxy)acetyl] [DesaminoHis7,Glu22,Arg26, Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl] cyclohexanecarbonyl}amino) butyrylamino]ethoxy}ethoxy) acetylamino]ethoxy} ethoxy) acetyl] [DesaminoHis7,Glu22,Arg26,Arg34, Lys37]GLP-1-(7-37); N-epsilon37-[2-(2-{2-[2-(2-{2-[(S)-4-carboxy-4-({trans-4-[(19-carboxy-nonadecanoylamino) methyl] cyclohexanecarbonyl}amino)butyrylamino]ethoxy}ethoxy)

acetylamino] ethoxy}ethoxy)acetyl] [DesaminoHis7,Glu22, Arg26,Glu30,Arg34, Lys37]GLP-1-(7-37); N-epsilon37-[2-(2-{2-[(S)-4-carboxy-4-((S)-4-carboxy-4-{12-[4-(16-(1H-tetrazol-5-yl)hexadecanoylsulfamoyl) butyrylamino] dodecanoylamino} butyrylamino) butyrylamino] ethoxy}ethoxy)acetyl] [Aib8,Glu22,Arg26,Arg34,Lys37] GLP-1-(7-37)amide; N-epsilon37-[2-(2-{2-[(S)-4-carboxy-4-((S)-4-carboxy-4-{12-[4-(16-(1H-tetrazol-5-yl)hexadecanoylsulfamoyl) butyrylamino] dodecanoylamino}butyrylamino) butyrylamino] ethoxy}ethoxy)acetyl] [DesaminoHis7,G1u22,Arg26, Arg34,Lys37]GLP-1-(7-37)amide; N-epsilon37-(3-((2-(2-(2-(2-Hexadecyloxyethoxy)ethoxy)ethoxy) ethoxy) ethoxy)) propionyl)[DesaminoHis7,Glu22,Arg26,Arg34, Lys37]GLP-1(7-37)-amide; N-epsilon37-{2-(2-(2-(2-[2-(2-(4-(hexadecanoylamino)-4-carboxybutyryl-amino)ethoxy) ethoxy] acetyl)ethoxy)ethoxy)acetyl)}-[desaminoHis7, Glu22,Arg26, Glu30,Arg34,Lys37] GLP-1-(7-37)amide; N-epsilon37-{2-(2-(2-(2-[2-(2-(4-(hexadecanoylamino)-4-carboxybutyryl-amino) ethoxy)ethoxy]acetyl)ethoxy) ethoxy) acetyl)}-[desaminoHis7,Glu22, Arg26, Arg34, Lys37]GLP-1-(7-37)amide; N-epsilon37-(2-(2-(2-(2-(2-(2-(2-(2-(octadecanoyl-amino)ethoxy)ethoxy) acetylamino) ethoxy) ethoxy)acetylamino) ethoxy)ethoxy) acetyl] [desaminoHis7,Glu22,Arg26,Arg34,Lys37] GLP-1 (7-37) amide; N-epsilon37-[4-(16-(1H-Tetrazol-5-yl) hexadecanoylsulfamoyl) butyryl] [DesaminoHis7,Glu22, Arg26, Arg34, Lys37]-GLP-1-(7-37)amide; N-epsilon37-[2-(2-{2-[2-(2-{2-[(S)-4-carboxy-4-(19-carboxynonadecanoylamino) butyrylamino] ethoxy}ethoxy) acetylamino]ethoxy} ethoxy)acetyl] [DesaminoHis7,Glu22, Arg26, Arg34,Lys37]GLP-1-(7-37); N-epsilon37-(2-{2-[2-((S)-4-carboxy-4-{(S)-4-carboxy-4-[(S)-4-carboxy-4-(19-carboxy-nonadecanoylamino)butyrylamino]butyrylamino} butyrylamino)ethoxy]ethoxy} acetyl)[DesaminoHis7, Glu22,Arg26,Arg34,Lys37]GLP-1-(7-37); N-epsilon37-{2-[2-(2-{(S)-4-[(S)-4-(12-{4-[16-(2-tert-Butyl-2H-tetrazol-5-yl)-hexadecanoylsulfamoyl] butyrylamino}dodecanoylamino)-4-carboxybutyrylamino]-4-carboxybutyrylamino} ethoxy)ethoxy]acetyl}[Desamino-His7,Glu22,Arg26,Arg34,Lys37] GLP-1 (7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22, Arg26, Arg34,Lys37]GLP-1-(7-37); N-alpha37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22,Arg26, Arg34,Lys37,epsilon-Lys37] GLP-1-(7-37)peptide; N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [desaminoHis7, Glu22,Arg26,Arg34,Lys37] GLP-1-(7-37); N-epsilon36-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl [desaminoHis7, Glu22,Arg26,Glu30,Arg34,Lys36] GLP-1-(7-37)-Glu-Lys peptide; N-epsilon37-[2-(2-{2-[2-(2-{2-[(S)-4-carboxy-4-({trans-4-[(19-carboxynonadecanoylamino) methyl]cyclohexanecarbonyl}amino)butyrylamino] ethoxy}ethoxy)acetylamino]ethoxy}ethoxy)acetyl][Aib8, Glu22,Arg26,Arg34,Lys37]GLP-1-(7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl]-[Aib8,Glu22, Arg26, Arg34,Aib35,Lys37]GLP-1(7-37); N-epsilon37-[(S)-4-carboxy-4-(2-{2-[2-(2-{2-[2-(17-carboxyheptadecanoylamino) ethoxy] ethoxy} acetylamino] ethoxy} ethoxy) acetylamino) butyryl] [Aib8,Glu22,Arg26, 34,Lys37] GLP-1 (7-37); N-epsilon37-[2-(2-[2-(2-[2-(2-[4-(17-carboxyheptadecanoylamino)-4-(S)-carboxybutyrylamino]ethoxy)ethoxy]acetylamino)ethoxy]ethoxy)acetyl] [ImPr7,Glu22, Arg26,34,Lys37], GLP-1-(7-37); N-epsilon26-{2-[2-(2-{2-[2-(2-{(S)-4-carboxy-4-[10-(4-carboxyphenoxy) decanoylamino]butyrylamino}ethoxy)ethoxy] acetylamino}ethoxy) ethoxy]acetyl}, N-epsilon37-{2-[2-(2-{2-[2-(2-{(S)-4-carboxy-4-[10-(4-carboxyphenoxy) decanoylamino] butyrylamino}ethoxy)ethoxy] acetylamino}ethoxy) ethoxy]acetyl}-[Aib8,Arg34,Lys37] GLP-1(7-37)-OH; N-epsilon26 (17-carboxyheptadecanoyl)-[Aib8,Arg34]GLP-1-(7-37)-peptide; N-epsilon26-(19-carboxynonadecanoyl)-[Aib8,Arg34]GLP-1-(7-37); N-epsilon26-(4-{[N-(2-carboxyethyl)-N-(15-carboxypentadecanoyl)amino]methyl}benzoyl[Arg34]GLP-1-(7-37); N-epsilon26-[2-(2-[2-(2-[2-(2-[4-(17-carboxyheptadecanoylamino)-4-(S)-carboxybutyrylamino]ethoxy)ethoxy] acetylamino) ethoxy]ethoxy)acetyl][Aib8,Arg34]GLP-1-(7-37); N-epsilon26-[2-(2-[2-(2-[2-(2-[4-(19-carboxynonadecanoylamino)-4-(S)-carboxybutyrylamino]ethoxy)ethoxy] acetylamino)ethoxy]ethoxy)acetyl][Aib8,Arg34]GLP-1-(7-37); N-epsilon26-[2-(2-[2-(2-[2-(2-[4-(17-carboxyheptadecanoylamino)-4-(S)-carboxybutyrylamino]ethoxy)ethoxy] acetylamino)ethoxy]ethoxy)acetyl][3-(4-Imidazolyl)Propionyl7,Arg34]GLP-1-(7-37); N-epsilon26-[2-(2-[2-(2-[2-(2-[4-(17-carboxyheptadecanoylamino)-(carboxymethylamino)acetylamino]ethoxy)ethoxy]acetylamino)ethoxy] ethoxy)acetyl][Aib8,Arg34]GLP-1-(7-37); N-epsilon26-[2-(2-[2-(2-[2-(2-[4-(17-carboxyheptadecanoylamino)-3(S)-Sulfopropionylamino]ethoxy)ethoxy]acetylamino)ethoxy] ethoxy)acetyl][Aib8,Arg34]GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Gly8,Arg34] GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Aib8,Arg34]GLP-1-(7-37)-amide; N-epsilon26-[2-(2-[2-(2-[2-(2-[4-(17-carboxyheptadecanoylamino)-4(S)-carboxybutyrylamino]ethoxy)ethoxy] acetylamino)ethoxy]ethoxy)acetyl] [Aib8,Arg34,Pro37] GLP-1-(7-37)amide; Aib8,Lys26(N-epsilon26-{2-(2-(2-(2-[2-(2-(4-(pentadecanoylamino)-4-carboxybutyrylamino] ethoxy)ethoxy]acetyl)ethoxy) ethoxy)acetyl)}), Arg34) GLP-1 H(7-37)-OH; N-epsilon26-[2-(2-[2-(2-[2-(2-[4-{[N-(2-carboxyethyl)-N-(17-carboxyheptadecanoyl)amino] methyl}benzoyl)amino]ethoxy) ethoxy]acetylamino) ethoxy]ethoxy)acetyl][Aib8,Arg34]GLP-1(7-37); N-alpha7-formyl, N-epsilon26-[2-(2-[2-(2-[2-(2-[4-(17-carboxyheptadecanoyl-amino)-4(S)-carboxybutyrylamino] ethoxy]ethoxy]acetylamino)ethoxy]ethoxy)acetyl] [Arg34] GLP-1-(7-37); N-epsilon2626-[2-(2-[2-(2-[2-(2-[4-(17-carboxyheptadecanoylamino)-4(S)-carboxybutyrylamino] ethoxy]ethoxy]acetylamino)ethoxy]ethoxy)acetyl][Aib8, Glu22, Arg34] GLP-1-(7-37); N-epsilon26{3-[2-(2-{2-[2-(2-[2-(2-[4-(15-(N-((S)-1,3-dicarboxypropyl) carbamoyl)pentadecanoylamino)-(S)-4-carboxybutyrylamino] ethoxy)ethoxy] ethoxy}ethoxy)ethoxy]ethoxy}ethoxy) ethoxy]propionyl} [Aib8,Arg34]GLP-1-(7-37); N-epsilon26-[2-(2-[2-(2-[2-(2-[4-{[N-(2-carboxyethyl)-N-(17-carboxyheptadecanoyl)amino]methyl}benzoyl)amino](4(S)-carboxybutyryl-amino)ethoxy) ethoxy]acetylamino)ethoxy) acetyl][Aib8,Arg34] GLP-1(7-37); N-epsilon26-{(S)-4-carboxy-4-((S)-4-carboxy-4-((S)-4-carboxy-4-((S)-4-carboxy-4-(19-carboxynonadecanoylamino)butyrylamino) butyrylamino)butyrylamino) butyrylamino} [Aib8,Arg34] GLP-1-(7-37); N-epsilon26-4-(17-carboxyheptadecanoylamino)-4(S)-carboxybutyryl-[Aib8,Arg34]GLP-1-(7-37); N-epsilon26-{3-[2-(2-{2-[2-(2-{2-[2-(2-[4-(17-carboxyheptadecanoylamino)-4(S)-carboxybutyrylamino]ethoxy)ethoxy]ethoxy} ethoxy)ethoxy]ethoxy}ethoxy)ethoxy]propionyl}[Aib8,Arg34]GLP-1-(7-37); N-epsilon26-{2-(2-(2-(2-[2-(2-(4-(17-carboxyheptadecanoylamino)-4-carboxybutyrylamino) ethoxy)ethoxy]acetyl)ethoxy)ethoxy)acetyl)}-[Aib8,22,27,30,35,Arg34,Pro37, Lys26] GLP-1 (7-37)amide; N-epsilon26-[2-(2-[2-[4-(21-carboxyuneicosanoylamino)-4(S)-carboxybutyrylamino]ethoxy]ethoxy)acetyl][Aib8,Arg34]GLP-1-(7-37); and N-epsilon26-[2-(2-[2-(2-[2-(2-[4-(21-carboxyuneicosanoylamino)-4(S)-carboxybutyrylamino]ethoxy]ethoxy]acetylamino)ethoxy]ethoxy)acetyl][Aib8,Arg34]GLP-1-(7-37).

Delivery Agent: Salt of N-(8-(2-hydroxybenzoyl)amino)caprylic acid

The delivery agent used in the present invention is a salt of N-(8-(2-hydroxybenzoyl)amino)caprylic acid. The structural formula of N-(8-(2-hydroxybenzoyl)amino)caprylate is shown in formula (I).

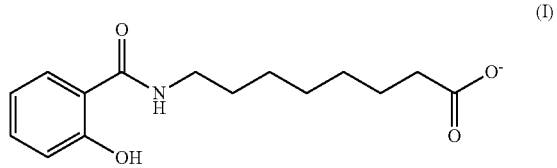 [SMILES: O=C([O-])CCCCCCCNC(=O)c1ccccc1O]

(I)

In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl)amino)caprylic acid is selected from the group consisting of the sodium salt, potassium salt and calcium salt of of N-(8-(2-hydroxybenzoyl)amino)caprylic acid.

Salts of N-(8-(2-hydroxybenzoyl)amino)caprylate may be prepared using the method described in e.g. WO96/030036, WO00/046182, WO01/092206 or WO2008/028859.

The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino) caprylic acid as well as combinations thereof. In some embodiments the delivery agent is a salt of N-(8-(2-hydroxybenzoyl)amino) caprylic acid as described in WO2007/121318.

In some embodiments the delivery agent is sodium N-(8-(2-hydroxybenzoyl)amino)caprylate (referred to as "SNAC" herein), also known as sodium 8-(salicyloylamino) octanoate.

In some embodiments the amount of the salt of N-(8-(2-hydroxybenzoyl) amino)caprylic acid in the composition is at least 0.6 mmol, such as selected from the group consisting of at least 0.65 mmol, at least 0.7 mmol, at least 0.75 mmol, at least 0.8 mmol, at least 0.8 mmol, at least 0.9 mmol, at least 0.95 mmol and at least 1 mmol. In some embodiments the amount of the salt of N-(8-(2-hydroxybenzoyl) amino) caprylic acid in the composition is in the range of 0.6-2.1 mmol or 0.6-1.9 mmol. In some embodiments the amount of the salt of N-(8-(2-hydroxybenzoyl) amino)caprylic acid in the composition is in the range of 0.7-1.7 mmol or 0.8-1.3 mmol. In some embodiments the amount of the salt of N-(8-(2-hydroxybenzoyl)amino)caprylic acid in the composition is up to 2.1 mmol, such as selected from the group consisting of up to 2.1 mmol, up to 2 mmol, up to 1.9 mmol, up to 1.8 mmol, up to 1.7 mmol, up to 1.6 mmol, up to 1.5 mmol, up to 1.4 mmol, up to 1.3 mmol, up to 1.2 mmol and up to 1.1 mmol. In some embodiments the amount of the salt of N-(8-(2-hydroxybenzoyl)amino)caprylic acid is 1 mmol, such as 1.08 mmol.

In some embodiments the amount of SNAC in the composition is at least 175 mg, such as an amount selected from the group consisting of at least 200 mg, at least 210 mg, at least 220 mg, at least 230 mg, at least 240 mg, at least 250 mg, at least 260 mg, at least 270 mg and at least 280 mg. In some embodiments the amount of SNAC in the composition is in the range of 175-575 mg, such as 200-500 mg or 250-400 mg. In some embodiments the amount of SNAC in the composition is up to 575 mg, such as an amount selected from the group consisting of up to 550 mg, up to 525 mg, up to 500 mg, up to 475 mg, up to 450 mg, up to 425 mg, up to 400 mg, up to 375 mg, up to 350 mg and up to 325 mg. In some embodiments the amount of SNAC in the composition is 300 mg.

In some embodiments the molar ratio between GLP-1 agonist and delivery agent in the composition is less than 10, such as less than 5 or less than 1.

Composition

The composition of the present invention is a solid composition and is administered by the oral route.

In some embodiments the composition comprises at least one pharmaceutically acceptable excipient. The term "excipient" as used herein broadly refers to any component other than the active therapeutic ingredient(s). The excipient may be an inert substance, an inactive substance, and/or a not medicinally active substance. The excipient may serve various purposes, e.g. as a carrier, vehicle, filler, binder, lubricant, glidant, disintegrant, flow control agents, crystallization retarders, solubilizers, stabilizer, colouring agent, flavouring agent, surfactant, emulsifier and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005). In some embodiments the excipients may be selected from binders, such as polyvinyl pyrrolidone (povidone), etc.; fillers such as cellulose powder, microcrystalline cellulose, cellulose derivatives like hydroxymethylcellulose, hydroxyethylcellulose, hydroxypropylcellulose and hydroxy-propylmethylcellulose, dibasic calcium phosphate, corn starch, pregelatinized starch, etc.; lubricants and/or glidants such as stearic acid, magnesium stearate, sodium stearylfumarate, glycerol tribehenate, etc.; flow control agents such as colloidal silica, talc, etc.; crystallization retarders such as Povidone, etc.; solubilizers such as Pluronic, Povidone, etc.; colouring agents, including dyes and pigments such as Iron Oxide Red or Yellow, titanium dioxide, talc, etc.; pH control agents such as citric acid, tartaric acid, fumaric acid, sodium citrate, dibasic calcium phosphate, dibasic sodium phosphate, etc.; surfactants and emulsifiers such as Pluronic, polyethylene glycols, sodium carboxymethyl cellulose, polyethoxylated and hydrogenated castor oil, etc.; and mixtures of two or more of these excipients and/or adjuvants.

In some embodiments the composition comprises at least 60% (w/w) delivery agent, less than 10% (w/w) binder, 5-40% (w/w) filler, and less than 10% (w/w) lubricant or glidant.

In some embodiments the composition comprises at least 60% (w/w), such as at least 70% (w/w) or at least 75% (w/w), delivery agent.

In some embodiments the composition comprises 0.1-10% (w/w), such as 0.2-4% (w/w) or 0.5-3% (w/w), of binder. In some embodiments the composition comprises 1% (w/w) or 2% (w/w) of binder. The composition may comprise a binder, such as povidone; starches; celluloses and derivatives thereof, such as microcrystalline cellulose, e.g., AVICEL PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be selected from the group consisting of dry binders and/or wet granulation binders. Suitable dry binders are, e.g., cellulose powder and microcrystalline cellulose, such as Avicel PH 102 and Avicel PH 200. In some embodiments the composition comprises avicel, such as avicel PH 102. Suitable binders for wet granulation or dry granulation are corn starch, polyvinyl pyrrolidone (povidon), vinylpyrrolidone-vinylacetate copolymer (copovidone) and cellulose derivatives like hydroxymethylcellulose, hydroxyethylcellulose, hydroxypropylcellulose and hydroxyl-propylmethylcellulose. In some embodiments the composition comprises povidone.

In some embodiments the composition comprises 5-40% (w/w), such as 10-30% (w/w) or 5-25% (w/w), of filler. In some embodiments the composition comprises 10.9% (w/w) or 18% (w/w) of filler, or comprises 19.5% (w/w) or 20.5 (w/w) of filler. The filler may be selected from lactose, mannitol, erythritol, sucrose, sorbitol, calcium phosphate, such as calciumhydrogen phosphate, microcrystalline cellulose, powdered cellulose, confectioner's sugar, compressible sugar, dextrates, dextrin and dextrose. In some embodiments the composition comprises microcrystalline cellulose, such as Avicel PH 102 or Avicel PH 200.

In some embodiments the composition comprises 0.1-10% (w/w) or 0.5-5% (w/w), such as 1-3.5% (w/w) or 1% (w/w), of lubricant and/or a glidant. In some embodiments the composition comprises a lubricant and/or a glidant, such as talc, magnesium stearate, calcium stearate, zinc stearate, glyceryl behenate, polyethylene oxide polymers, sodium lauryl sulfate, magnesium lauryl sulfate, sodium oleate, sodium stearyl fumarate, stearic acid, hydrogenated vegetable oils, silicon dioxide and/or polyethylene glycol. In some embodiments the composition comprises magnesium stearate.

In some embodiments the composition comprises a disintegrant, such as sodium starch glycolate, polacrilin potassium, sodium starch glycolate, crospovidon, croscarmellose, sodium carboxymethylcellulose or dried corn starch.

The composition may comprise one or more surfactants, for example a surfactant, at least one surfactant, or two different surfactants. The term "surfactant" refers to any molecules or ions that are comprised of a water-soluble (hydrophilic) part, and a fatsoluble (lipophilic) part. The surfactant may e.g. be selected from the group consisting of anionic surfactants, cationic surfactants, nonionic surfactants, and/or zwitterionic surfactants.

Still further, the composition may be formulated as is known in the art of oral formulations of insulinotropic compounds, e.g. using any one or more of the formulations described in WO 2008/145728.

A composition may also be used in the formulation of site specific, controlled, sustained, protracted, prolonged, delayed, pulsatile, retarded, and/or slow release drug delivery systems.

The composition of the invention may be prepared as is known in the art.

The composition may be administered in several dosage forms, for example as a tablet; a coated tablet; a chewing gum; a capsule such as hard or soft gelatine capsules or a powder. The composition may further be compounded in a drug carrier or drug delivery system, e.g. in order to improve stability and/or solubility or further improve bioavailability. The composition may be a freeze-dried or spray-dried composition.

The composition may be in the form of a tablet. In some embodiments the weight of the tablet is in the range of 175 mg to 1000 mg, such as in the range of 175-250 mg, 300-500 mg or 500-900 mg, or such as about 200 mg, about 400 mg or about 700 mg. In some embodiments the weight of the tablet is in the range of 200 mg to 1000 mg, such as in the range of 500-700 mg or 600-1000 mg, or such as about 200 mg, about 400 mg, about 600 mg or about 800 mg.

In some embodiments the composition may be granulated prior to being compacted. The composition may comprise an intragranular part and an extragranular part, wherein the intragranular part has been granulated and the extragranular part has been added after granulation. The intragranular part may comprise the GLP-1 agonist, the delivery agent and a binder. In some embodiments the intragranular part comprises povidone. The extragranular part may comprise a filler, a lubricant and/or a glidant. In some embodiments the extragranular part comprises microcrystalline cellulose, such as avicel, e.g. avicel PH120 or avicel PH200. In some embodiments the extragranular part comprises magnesium stearate.

To prepare a dry blend of tabletting material, the various components are weighed, optionally delumped and then combined. The mixing of the components may be carried out until a homogeneous blend is obtained.

If granules are to be used in the tabletting material, granules may be produced in a manner known to a person skilled in the art, for example using wet granulation methods known for the production of "built-up" granules or "broken-down" granules. Methods for the formation of built-up granules may operate continuously and comprise, for example simultaneously spraying the granulation mass with granulation solution and drying, for example in a drum granulator, in pan granulators, on disc granulators, in a fluidized bed, by spray-drying or spray-solidifying, or operate discontinuously, for example in a fluidized bed, in a rotary fluid bed, in a batch mixer, such as a high shear mixer or a low shear mixer, or in a spray-drying drum. Methods for the production of broken-down granules, which may be carried out discontinuously and in which the granulation mass first forms a wet aggregate with the granulation solution, which is subsequently comminuted or by other means formed into granules of the desired size and the granules may then be dried. Suitable equipment for the granulation step are planetary mixers, low shear mixers, high shear mixers, extruders and spheronizers, such as an apparatus from the companies Loedige, Glatt, Diosna, Fielder, Collette, Aeschbach, Alexanderwerk, Ytron, Wyss & Probst, Werner & Pfleiderer, HKD, Loser, Fuji, Nica, Caleva and Gabler. Granules may be also formed by dry granulation techniques in which the pharmaceutically active agent is compressed with the excipients to form relatively large moldings, for example slugs or ribbons, which are comminuted by grinding, and the ground material serves as the tabletting material to be later compacted. Suitable equipment for dry granulation is roller compaction equipment from Gerteis, such as Gerteis MINI-PACTOR.

To compact the tabletting material into a solid oral dosage form, for example a tablet, a tablet press may be used. In a tabletting press, the tabletting material is filled (e.g. force fed or gravity fed) into a die cavity. The tabletting material is then compacted by a punch with pressure. Subsequently, the resulting compact, or tablet is ejected from the tabletting press. The above mentioned compaction process is subsequently referred to herein as the "compaction process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom).

In some embodiments the method of preparation of the tablet comprises a) wet granulation of a mixture comprising the GLP-1 agonist, the delivery agent and a binder; b) optionally drying the wet granulate; c) blending of the dried wet granulates with at least a filler and at least a lubricant or a glidant, and then d) compression of the blend into tablets. The granulation may be a wet granulation or a dry granulation.

Disintegration time: In some embodiments the disintegration time of the tablet is in the range of 7 minutes to 15 minutes, such as in the range of 8 minutes to 13 minutes. Disintegration time may be determined using a Pharma Test PTZ AUTO disintegration test apparatus. The disintegration apparatus consists of a basket rack holding 2×6 plastic tubes, open at the top and bottom, the bottom of the tube is covered by a screen. Tablets are placed in the tubes and on top of the tablets are placed discs for automated disintegration detection. The basket is immersed in 800 ml purified water maintained at 37° C., in a 1 L beaker. Time for complete disintegration is measured. Furthermore, tablets may be observed visually for surface eroding behaviour during the disintegration test.

In some embodiments the tablet of the invention co-releases the active ingredients and the delivery agent by surface erosion; hence, the tablets becomes smaller and smaller with time by dissolution primarily from the surface from non-disintegrated tablets. Concurrent release: In some embodiments the compositions show concurrent release of the GLP-1 agonist and the delivery agent from the surface of the tablet. This can be tested by visual inspection during the disintegration test; the tablets do not have concurrent release of the GLP-1 agonist and the delivery agent from the surface of the tablet if the tablet breaks into smaller parts during the first 8 minutes of the disintegration test.

Dissolution test: Another test for concurrent release of the GLP-1 agonist and the delivery agent is the dissolution test. Here, the rate of appearance (in percentage) of the GLP-1 agonist and the delivery agent is measured. The dissolution test may be carried out as described in the following: Dissolution is performed on a Varian 705 DS. The analysis is based on the pharmacopeia method Ph Eur 2.9.3, Apparatus 2 (Paddle apparatus). 100 ml mini vessel with mini-paddles is used, and paddle speed is 75 rpm. After 120 minutes, the paddle speed is changed to 250 rpm. The dissolution medium used for the dissolution test is 100 ml of 200 mM $KH_2PO_4$ (containing 0.07% Tween 80 to avoid the GLP-1 agonist from sticking to the wall of the bath and to the paddle), with pH 6.8. Samples are taken after 5, 15, 30, 45, 60, 120 and 135 minutes. The volume of the sample is 2 ml, and the sample is taken with a disposable syringe. After each sample is taken, the same volume (2 ml) of the dissolution medium is added to the bath, in order to keep the total volume of 100 ml constant. The sample is pressed through a 0.22 μm Millex®-GV filter. Finally, the samples are analysed for concentration of the GLP-1 agonist and for concentration of the delivery agent by UPLC.

Hardness test: The hardness of the tablets is measured with a Pharma Test (33AA02), which measures the force required to disrupt the tablet, and the test is based on the pharmacopeia method Ph Eur 2.9.8.

The treatment with a composition according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

Additional embodiments of the compositions of the invention are described in the section headed "particular embodiments" before the experimental section.

Pharmaceutical Indications

The present invention also relates to a composition of the invention for use as a medicament. In particular embodiments the composition of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix). In another particular embodiment, the indication is (i). In a further particular embodiment the indication is (v). In a still further particular embodiment the indication is (iix). In some embodiments the indications are type 2 diabetes and/or obesity.

Further Embodiments

1. A solid composition for oral administration comprising a GLP-1 agonist and a salt of N-(8-(2-hydroxybenzoyl)amino)caprylic acid, wherein the amount of said salt of N-(8-(2-hydroxybenzoyl)amino)caprylic acid is at least 0.6 mmol.

2. A solid composition for oral administration comprising a GLP-1 agonist and a salt of N-(8-(2-hydroxybenzoyl)amino)caprylic acid, wherein the amount of said salt of N-(8-(2-hydroxybenzoyl)amino)caprylic acid is at least 0.8 mmol.

Form of Composition

3. A composition according to any one of the preceding embodiments, wherein said composition is in the form of a tablet.

4. A composition according to any one of the preceding embodiments, wherein the tablet has a weight in the range of 175-1000 mg.

5. A composition according to any one of the preceding embodiments, wherein the tablet has a weight in the range of 200-800 mg.

6. A composition according to any one of the preceding embodiments, wherein the tablet has a weight selected from the group consisting of 200 mg, such as 400 mg or 700 mg.

7. A composition according to any one of the preceding embodiments, wherein the tablet has a weight selected from the group consisting of 200 mg, 400 mg, 600 mg or 800 mg.

Salt of N-(8-(2-hydroxybenzoyl)amino)caprylic acid

8. A composition according to any one of the preceding embodiments, wherein said salt of N-(8-(2-hydroxybenzoyl)amino)caprylic acid comprises one monovalent cation, two monovalent cations or one divalent cation.

9. A composition according to any one of the preceding embodiments, wherein said salt of N-(8-(2-hydroxybenzoyl)amino)caprylic acid is selected from the group consisting of the sodium salt, potassium salt and calcium salt of of N-(8-(2-hydroxybenzoyl)amino)caprylic acid.

10. A composition according to any one of the preceding embodiments, wherein said salt of N-(8-(2-hydroxybenzoyl)amino)caprylic acid is sodium N-(8-(2-hydroxybenzoyl)amino)caprylate (SNAC).

Amount of salt of N-(8-(2-hydroxybenzoyl)amino)caprylic acid

11. A composition according to any one of the preceding embodiments, wherein the amount of said salt of N-(8-(2-hydroxybenzoyl)amino)caprylic acid is in the range of 0.6-2.1 mmol, such as 0.6-1.9 mmol, 0.7-1.7 mmol or 0.8-1.3 mmol.

12. A composition according to any one of the preceding embodiments, wherein the amount of said salt of N-(8-(2-hydroxybenzoyl)amino)caprylic acid is at least 0.6 mmol, such as selected from the group consisting of at least 0.65 mmol, at least 0.7 mmol, at least 0.75 mmol, at least 0.8 mmol, at least 0.8 mmol, at least 0.9 mmol, at least 0.95 mmol and at least 1 mmol.

13. A composition according to any one of the preceding embodiments, wherein the amount of said salt of N-(8-(2-hydroxybenzoyl)amino)caprylic acid is up to 2.1 mmol, such as selected from the group consisting of up to 2.1 mmol, up to 2 mmol, up to 1.9 mmol, up to 1.8 mmol, up to 1.7 mmol, up to 1.6 mmol, up to 1.5 mmol, up to 1.4 mmol, up to 1.3 mmol, up to 1.2 mmol and up to 1.1 mmol.

14. A composition according to any one of the preceding embodiments, wherein the amount of said salt of N-(8-(2-hydroxybenzoyl)amino)caprylic acid is 1 mmol, such as 1.08 mmol.

15. A composition according to any one of the preceding embodiments, wherein said composition comprises at least 60% (w/w), such as at least 70% (w/w) or at least 75% (w/w), of said salt of N-(8-(2-hydroxybenzoyl) amino)caprylic acid.

Amount of SNAC

16. A composition according to embodiment 10, wherein the amount of SNAC is at least 175 mg, such as an amount selected from the group consisting of at least 200 mg, at least 210 mg, at least 220 mg, at least 230 mg, at least 240 mg, at least 250 mg, at least 260 mg, at least 270 mg and at least 280 mg.

17. A composition according to embodiment 10, wherein the amount of SNAC is up to 575 mg, such as an amount selected from the group consisting of up to 550 mg, up to 525 mg, up to 500 mg, up to 475 mg, up to 450 mg, up to 425 mg, up to 400 mg, up to 375 mg, up to 350 mg and up to 325 mg.

18. A composition according to embodiment 10, wherein the amount of SNAC is 300 mg.

GLP-1

19. A composition according to any one of the preceding embodiments, wherein the amount of the GLP-1 agonist is in the range of 0.01 mg to 100 mg.

20. A composition according to any one of the preceding embodiments, wherein the GLP-1 agonist comprises one substituent.

21. A composition according to any one of the preceding embodiments, wherein said substituent comprises a fatty acid or a fatty diacid.

22. A composition according to any one of the preceding embodiments, wherein said substituent comprises a C16, C18 or C20 fatty acid.

23. A composition according to any one of the preceding embodiments, wherein said substituent comprises a C16, C18 or C20 fatty diacid.

24. A composition according to any one of the preceding embodiments, wherein said substituent comprises formula (X)

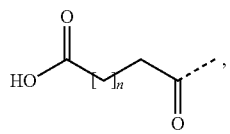

(X)

wherein n is at least 13, such as n is 13, 14, 15, 16, 17, 18 or 19.

25. A composition according to any one of the preceding embodiments, wherein said substituent comprises one or more 8-amino-3,6-dioxaoctanoic acid (OEG), such as two OEG.

26. A composition according to any one of the preceding embodiments, wherein the GLP-1 agonist is GLP-1 (7-37), GLP-1 (7-36)amide, exendin-4 or an analogue thereof comprising up to 10 substitutions, deletions, additions and/or insertions, wherein said GLP-1 agonist optionally comprises one substituent.

27. A composition according to any one of the preceding embodiments, wherein the GLP-1 agonist is GLP-1 (7-37), GLP-1 (7-36)amide, exendin-4 or an analogue thereof comprising up to 7 substitutions, deletions, additions and/or insertions, wherein said GLP-1 agonist optionally comprises one substituent.

28. A composition according to any one of the preceding embodiments, wherein the GLP-1 agonist is GLP-1 (7-37), GLP-1 (7-36)amide, exendin-4 or an analogue thereof comprising up to 4 substitutions, deletions, additions and/or insertions, wherein said GLP-1 agonist optionally comprises one substituent.

29. A composition according to any one of the preceding embodiments, wherein the GLP-1 agonist is GLP-1 (7-37), GLP-1 (7-36)amide, exendin-4 or an analogue thereof comprising up to 3 substitutions, deletions, additions and/or insertions, wherein said GLP-1 agonist optionally comprises one substituent.

30. A composition according to any one of the preceding embodiments, wherein the GLP-1 agonist is semaglutide.

31. A composition according to any one of the preceding embodiments, wherein the amount of the GLP-1 agonist is in the range of 1 to 20 mg, such as in the range of 5 to 20 mg, such as in the range of 5 to 15 mg, such as 10 mg.

32. A composition according to any one of the preceding embodiments, wherein the amount of GLP-1 is in the range of 0.05 to 25 μmol, such as in the range of 0.5 to 2.5 μmol.

Further Excipients

33. A composition according to any one of the preceding embodiments, wherein said composition comprises at least one additional pharmaceutically acceptable excipient.

34. A composition according to any one of the preceding embodiments, wherein said excipient is selected from one or more from the group consisting of binders, fillers, disintegrants and lubricants and/or glidants.

35. A composition according to any one of the preceding embodiments, wherein said composition comprises 0.1-10% (w/w), such as 0.2-4% (w/w) or 0.5-3% (w/w), of binder.

36. A composition according to any one of the preceding embodiments, wherein said composition comprises 1% (w/w) or 2% (w/w) of binder.

37. A composition according to any one of the preceding embodiments, wherein said binder is povidone.

38. A composition according to any one of the preceding embodiments, wherein said composition comprises 5-40% (w/w), such as 10-30% (w/w) or 5-25% (w/w), of filler.

39. A composition according to any one of the preceding embodiments, wherein said composition comprises 10.9% (w/w) or 18% (w/w) of filler, or comprises 19.5% (w/w) or 20.5% (w/w) of filler.

40. A composition according to any one of the preceding embodiments, wherein said filler is avicel, such as avicel PH 102 or avicel PH 200.

41. A composition according to any one of the preceding embodiments, wherein said composition comprises 0.1-10% (w/w) or 0.5-5% (w/w) lubricant and/or a glidant.
42. A composition according to any one of the preceding embodiments, wherein said composition comprises 1-3.5% (w/w) or 1% (w/w) lubricant and/or a glidant.
43. A composition according to any one of the preceding embodiments, wherein said excipient is magnesium stearate.
44. A composition according to any one of the preceding embodiments, wherein said composition comprises at least 60% (w/w) delivery agent, less than 10% (w/w) binder, 5-40% (w/w) filler, and less than 10% (w/w) lubricant and/or glidant.

Administration Regime

45. Use of a composition according to any one of the preceding embodiments, wherein the composition is administered orally.

Functional Features

46. A composition according to any one of the preceding embodiments, wherein said tablet has surface eroding properties.
47. A composition according to any one of the preceding embodiments, wherein said tablet has co-release of the GLP-1 agonist and the delivery agent as determined by the concurrent release test described herein.
48. A composition according to any one of the preceding embodiments, wherein said tablet has a disintegration time in the range of 7-15 minutes as determined by the disintegration test described herein.
49. A composition according to any one of the preceding embodiments, wherein said tablet has a hardness of at least 50 N as determined by the hardness test described herein.

Use as a Medicament

50. Use of a composition as defined in any one of the preceding embodiments in medicine.
51. Use of a composition as defined in any one of the preceding embodiments for treatment of type 2 diabetes or obesity.
52. A method for the treatment of type 2 diabetes or obesity comprising administering a composition as defined in any one of the preceding embodiments.

EXAMPLES

Example 1

The objective of the present study was to evaluate the oral bioavailability in beagle dogs of a series of compositions comprising semaglutide and SNAC.

Method

Animals, Dosing and Blood Sampling

Twenty four male and 24 female beagle dogs, weighing 6-11 kg during the study period were included in the study. The dogs were dosed in fasting state. The compositions were administered by a single oral dosing to the dogs in groups of 4 male and 4 females. Blood samples were taken at the following time points: predose, 0.25, 0.5, 0.75, 1, 1.5, 2, 2.5, 3, 4, 6, 8, 24, 48, 72, 96, 120, 144, 192 and 240 hours post dosing.

The i.v. solution (20 nmol/mL in a pH 7.4 solution comprising 0.1 mg/ml Tween 20, 5.5 mg/ml Phenol, 1.42 mg/ml Na2HPO4 and 14 mg/ml Propylene Glycol) was dosed in a dose volume of 0.1 mL/kg in the same dog colony in one dosing group (n=8). Blood samples were taken at the following time points: predose, 0.25, 0.5, 0.75, 1, 1.5, 2, 2.5, 3, 4, 6, 8, 24, 48, 72, 96, 120, 144, 192 and 240 hours post dosing.

Preparation of Plasma

All blood samples were collected into test tubes containing EDTA for stabilisation and kept on ice until centrifugation. Plasma was separated from whole blood by centrifugation and the plasma was stored at $-20°$ C. or lower until analysis.

Analysis of Plasma Samples

The plasma was analyzed for semaglutide using a Luminescence Oxygen Channeling Immunoassay (LOCI). The LOCI assay employs donor beads coated with streptavidin and acceptor beads conjugated with a monoclonal antibody binding to a midmolecular region of semaglutide. The other monoclonal antibody, specific for an N-terminal epitope, was biotinylated. In the assay the three reactants were combined with the semaglutide which form a two-sited immuno-complex. Illumination of the complex releases singlet oxygen atoms from the donor beads which channels into the acceptor beads and trigger chemiluminescence which was measured in the EnVision plate reader. The amount of light was proportional to the concentration of semaglutide and the lower limit of quantification (LLOQ) in plasma was 100 pM.

Analysis of Compositions

The amount of semaglutide and SNAC in the composition were assayed using a reversed-phase HPLC method, with UV detection at 230 nm, a linear gradient of mobile phases made up of deionised H2O:trifluoroacetic acid (TFA) (1000:1) (v/v) (A), and acetonitrile:TFA (1000:1) (v/v) (B).

Pharmacokinetic Calculations

Semaglutide plasma concentration data were subjected to non-compartmental pharmacokinetic analysis using the PC based software WinNonlin, v. 5.2 (Pharsight, Mountain View, Calif. 94041, USA). For each individual dog the maximum plasma concentration ($C_{max}$) and time for maximum plasma concentration ($t_{max}$) were read from the plasma concentration time curves. The following pharmacokinetic parameters were estimated: Area Under the Curve to infinity (AUCinf.), and AUCinf./Dose (AUCinf./D). Bioavailability (F) was calculated as the fraction absorbed (in %) based on the dose normalised AUC (AUCinf./D) following oral and intravenous administration. Summary statistics of pharmacokinetic results were presented as arithmetic mean with calculated standard deviation, also for $T_{max}$ and plasma half life.

Preparation of Compositions

Tablets with different amounts of SNAC (150, 300 and 600 mg) and semaglutide (5, 10, 15 and 20 mg) were prepared. The composition of the tablets is shown in Table 1.

TABLE 1

Tablet composition expressed as "per tablet"

| Composition | | A | B | C | D | E | F |
|---|---|---|---|---|---|---|---|
| Semaglutide (mg) | | 10 | 10 | 10 | 5 | 15 | 20 |
| SNAC (mg) | | 150 | 300 | 600 | 300 | 300 | 300 |
| Povidone (mg) | | 2 | 4 | 7 | 3.5 | 4 | 4 |
| Extra-granular | Avicel PH 102 (mg) | 36 | 82 | 76 | 38 | 77 | 72 |
| | Magesium Stearate (mg) | 2 | 4 | 7 | 3.5 | 4 | 4 |
| Tablet Weight (mg) | | 200 | 400 | 700 | 350 | 400 | 400 |

Semaglutide was prepared according to the method described in WO2006/097537, Example 4, and subsequently freeze-dried. SNAC was prepared according to the method described in WO2008/028859. The compositions were prepared using the following manufacturing process:

1) The ingredients were first screened through a #35 mesh;
2) semaglutide and SNAC were geometrically blended in a mortar and pestle;
3) povidone was dissolved in water and the resulting solution was used to granulate the blend of semaglutide and SNAC;
4) the granules were dried at a temperature not exceeding 40° C. to a moisture level of ≤4%; and
5) the resulting dried granules were milled through a #35 mesh;
6) finally, the granules were blended with the extra granular ingredients (see Table 1) and the final blend was compressed into tablets, wherein the compression was performed at a pressure of approximately 4.4 kN or higher.

The tablet hardness of was more than 50 N as determined by the Pharma Test (33AA02), which measures the force required to disrupt the tablet, and the test is based on the pharmacopeia method Ph Eur 2.9.8.

Results

Table 2 summarises the pharmacokinetic parameters for semaglutide from single dosing of the tablets shown in Table 1.

TABLE 2

Summary of pharmacokinetic parameters for semaglutide from single dosing of tablets comprising 10 mg semaglutide in combination with 150 mg (A), 300 mg (B) or 600 mg (C) SNAC.

| Composition | SNAC (mg) | $T_{max}$ (h) | $C_{max}$ (pM) | AUCinf./D | F (%) |
|---|---|---|---|---|---|
| A | 150 | 0.6 | 6222 | 0.62 | 0.17 |
| B | 300 | 0.8 | 21871 | 2.335 | 0.63 |
| C | 600 | 1.1 | 9972 | 1.09 | 0.29 |

Individual and mean (SD) calculated pharmacokinetic parameters following oral dosing appear from Tables 3 to 5 and following intravenous administration appear from Table 6.

TABLE 3

Pharmacokinetic parameters for semaglutide following oral dosing of the combination of 10 mg semaglutide and 150 mg SNAC (Composition A) to 4 male and 4 female Beagle dogs.

| Dog no | Dose (nmol/kg) | $T_{max}$ (h) | $C_{max}$ (pM) | AUCinf./D (h*kg*pmol/l/pmol) | F (%) |
|---|---|---|---|---|---|
| 1025 | 285 | 1.5 | 38300 | 4.08 | 1.1 |
| 1026 | 548 | n.a. | 0 | 0 | 0 |
| 1027 | 278 | 0.2 | 228 | 0 | 0.00003 |
| 1028 | 338 | 2.0 | 3410 | 0.31 | 0.08 |
| 1029 | 246 | n.a. | 0 | 0 | 0 |
| 1030 | 244 | 0.2 | 2030 | 0.07 | 0.02 |
| 1031 | 223 | n.a. | 0 | 0 | 0 |
| 1032 | 254 | 0.5 | 5810 | 0.47 | 0.13 |
| Mean | 302 | 0.6 | 6222 | 0.62 | 0.17 |
| SD | 105 | 0.5 | 13130 | 1.41 | 0.38 | n.a.) not analysed

TABLE 4

Pharmacokinetic parameters for semaglutide following oral dosing of oral dosing of the combination of 10 mg semaglutide and 300 mg SNAC (Composition B) to 4 male and 4 female Beagle dogs.

| Dog no | Dose (nmol/kg) | $T_{max}$ (h) | $C_{max}$ (pM) | AUCinf./D (h*kg*pmol/l/pmol) | F (%) |
|---|---|---|---|---|---|
| 1033 | 294 | 0.5 | 5540 | 0.35 | 0.09 |
| 1034 | 301 | 2.0 | 72000 | 6.83 | 1.8 |
| 1035 | 276 | n.a. | 0 | 0 | 0 |
| 1036 | 258 | 1.5 | 21100 | 2.52 | 0.68 |
| 1037 | 239 | 2.0 | 70000 | 8.73 | 2.3 |
| 1038 | 261 | 0.7 | 4050 | 0.28 | 0.07 |
| 1039 | 223 | 0.5 | 2010 | 0.07 | 0.02 |
| 1040 | 249 | 0.2 | 271 | 0.00 | 0.0001 |
| Mean | 263 | 0.8 | 21871 | 2.35 | 0.63 |
| SD | 26.7 | 0.5 | 31061 | 3.49 | 0.94 | n.a.) not analysed

TABLE 5

Pharmacokinetic parameters for semaglutide following oral dosing of the combination of 10 mg semaglutide and 600 mg SNAC (Composition C) to 4 male and 4 female Beagle dogs.

| Dog no | Dose (nmol/kg) | $T_{max}$ (h) | $C_{max}$ (pM) | AUCinf./D (h*kg*pmol/l/pmol) | F (%) |
|---|---|---|---|---|---|
| 1041 | 262 | n.a. | 0 | 0 | 0 |
| 1042 | 278 | 0.5 | 1890 | 0.52 | 0.14 |
| 1043 | 265 | 3.0 | 261 | 0 | 0.0005 |
| 1044 | 265 | 0.7 | 1270 | 0.02 | 0.01 |
| 1045 | 251 | 1.5 | 48400 | 5.2 | 1.4 |
| 1046 | 285 | 2.0 | 22900 | 2.53 | 0.68 |
| 1047 | 226 | 0.7 | 4100 | 0.4 | 0.11 |
| 1048 | 248 | 0.7 | 953 | 0.01 | 0.004 |
| Mean | 260 | 1.1 | 9972 | 1.09 | 0.29 |
| SD | 18 | 0.5 | 17298 | 1.87 | 0.50 | n.a.) not analysed

TABLE 6

Pharmacokinetic parameters for semaglutide following intravenous dosing of 2 nmol/kg semaglutide to 4 male and 4 female Beagle dogs.

| Dog no | Dose (pmol/kg) | $T_{max}$ (h) | $C_{max}$ (pM) | AUCinf./D (h*kg*pmol/l/pmol) |
|---|---|---|---|---|
| 1065 | 1980 | 0.5 | 31400 | 310 |
| 1066 | 1980 | 0.2 | 17400 | 227 |
| 1067 | 1980 | 0.2 | 28300 | 385 |
| 1068 | 1980 | 4.0 | 12900 | 384 |
| 1069 | 1980 | 0.2 | 28300 | 398 |
| 1070 | 1980 | 0.2 | 27400 | 383 |
| 1071 | 1980 | 0.2 | 31000 | 472 |
| 1072 | 1980 | 0.2 | 25700 | 418 |
| Mean | 1980 | 0.8 | 25300 | 372 |
| SD | 0 | 1.3 | 6638 | 73.8 |

TABLE 7

Summary of pharmacokinetic parameters for semaglutide from single dosing of composition comprising 300 mg SNAC in combination with 5, 10, 15 or 20 mg semaglutide.

| Composition | SNAC (mg) | Semaglutide (mg) | $T_{max}$ (h) | $C_{max}$ (pM) | AUCinf./D | F (%) |
|---|---|---|---|---|---|---|
| D | 300 | 5 | 0.5 | 4446 | 1.22 | 0.33 |
| B | 300 | 10 | 0.8 | 21871 | 2.33 | 0.63 |

TABLE 7-continued

Summary of pharmacokinetic parameters for semaglutide from single dosing of composition comprising 300 mg SNAC in combination with 5, 10, 15 or 20 mg semaglutide.

| Composition | SNAC (mg) | Semaglutide (mg) | $T_{max}$ (h) | $C_{max}$ (pM) | AUCinf./D | F (%) |
|---|---|---|---|---|---|---|
| E | 300 | 15 | 1.0 | 42612 | 4.61 | 1.2 |
| F | 300 | 20 | 1.3 | 9603 | 5.09 | 1.4 |

TABLE 8

Pharmacokinetic parameters for semaglutide following oral dosing of the combination of 5 mg semaglutide and 300 mg SNAC (Composition D) to 4 male and 4 female Beagle dogs.

| Dog no | Dose (nmol/kg) | $T_{max}$ (h) | $C_{max}$ (pM) | AUCinf./D (h*kg*pmol/l/pmol) | F (%) |
|---|---|---|---|---|---|
| 1049 | 123 | 1 | 4490 | 1.54 | 0.41 |
| 1050 | 153 | 0.7 | 4420 | 0.5 | 0.13 |
| 1051 | 114 | 1 | 17200 | 4.27 | 1.1 |
| 1052 | 131 | 0.2 | 2390 | 0.52 | 0.14 |
| 1053 | 119 | 0.5 | 1860 | 0.31 | 0.08 |
| 1054 | 131 | 0.2 | 575 | 0.03 | 0.01 |
| 1055 | 113 | 0.7 | 3210 | 0.45 | 0.12 |
| 1056 | 107 | 0.5 | 1420 | 2.16 | 0.58 |
| Mean | 124 | 0.5 | 4446 | 1.22 | 0.33 |
| SD | 15 | 0.5 | 5335 | 1.42 | 0.38 |

TABLE 9

Pharmacokinetic parameters for semaglutide following oral dosing of the combination of 15 mg semaglutide and 300 mg SNAC (Composition E) to 6 Beagle dogs.

| Dog no | Dose (nmol/kg) | $T_{max}$ (h) | $C_{max}$ (pM) | AUCinf./D (h*kg*pmol/l/pmol) | F (%) |
|---|---|---|---|---|---|
| 1067 | 318 | 1 | 56500 | 5.18 | 1.4 |
| 1068 | 393 | 1.5 | 61000 | 4.75 | 1.3 |
| 1069 | 322 | 1 | 15100 | 1.23 | 0.3 |
| 1070 | 341 | 0.5 | 2090 | 0 | 0.01 |
| 1071 | 283 | 2.5 | 114000 | 16.00 | 4.3 |
| 1072 | 312 | 0.5 | 6980 | 0.47 | 0.1 |
| Mean | 328 | 1.0 | 42612 | 4.61 | 1.2 |
| SD | 37 | 0.8 | 43118 | 6.00 | 1.6 |

TABLE 10

Pharmacokinetic parameters for semaglutide following oral dosing of the combination of 20 mg semaglutide and 300 mg SNAC (Composition F) to 4 male and 4 female Beagle dogs.

| Dog no | Dose (nmol/kg) | $T_{max}$ (h) | $C_{max}$ (pM) | AUCinf./D (h*kg*pmol/l/pmol) | F (%) |
|---|---|---|---|---|---|
| 1057 | 588 | 1 | 197000 | 9.60 | 2.6 |
| 1058 | 619 | 1.5 | 144000 | 7.11 | 1.9 |
| 1059 | 508 | 1.5 | 77400 | 4.45 | 1.2 |
| 1060 | 519 | 1.5 | 91900 | 5.18 | 1.4 |
| 1061 | 519 | 2 | 70400 | 4.72 | 1.3 |
| 1062 | 519 | 1.5 | 155000 | 9.09 | 2.4 |
| 1063 | 460 | 0.7 | 1620 | 0.01 | 0.004 |
| 1064 | 487 | 1.5 | 11500 | 0.61 | 0.16 |
| Mean | 527 | 1.3 | 93603 | 5.09 | 1.4 |
| SD | 52 | 0.5 | 68667 | 3.52 | 0.95 |

Conclusion

Surprisingly, tablets comprising 300 mg SNAC showed improved bioavailability in the current study compared to tablets comprising 150 mg or 600 mg SNAC.

The invention claimed is:

1. A solid composition for oral administration comprising a GLP-1 agonist, a salt of N-(8-(2-hydroxybenzyol)amino) caprylic acid, and at least one excipient selected from the group consisting of a lubricant, binder, and filler;
   wherein the GLP-1 agonist is semaglutide; and
   wherein the composition comprises at least 60% (w/w) of the salt of N-(8-(2-hydroxybenzyol)amino)caprylic acid.

2. The composition according to claim 1, wherein the composition is in the form of a tablet.

3. The composition according to claim 1, wherein the salt of N-(8-(2-hydroxybenzyol)amino)caprylic acid is sodium N-(8-(2-hydroxybenzyol)amino)caprylate (SNAC).

4. The composition according to claim 1, wherein the amount of the salt of N-(8-(2-hydroxybenzyol)amino) caprylic acid is in the range of 0.6-2.1 mmol.

5. The composition according to claim 1, wherein the amount of the semaglutide is in the range of 0.01 mg to 100 mg.

6. The composition according to claim 1, wherein the amount of the semaglutide is in the range of 0.01 to 25 μmol.

7. The composition according to claim 1, wherein the lubricant is magnesium stearate.

8. The composition according to claim 1, wherein the binder is povidone.

9. The composition according to claim 1, wherein the filler is microcrystalline cellulose.

* * * * *